(12) United States Patent
Coursey et al.

(10) Patent No.: US 9,861,985 B2
(45) Date of Patent: Jan. 9, 2018

(54) SLUG CONTROL DURING THERMAL CYCLING

(75) Inventors: Johnathan S. Coursey, Germantown, MD (US); Kenton C. Hasson, Germantown, MD (US); Sami Kanderian, Germantown, MD (US); Gregory H. Owen, Clarksburg, MD (US); Hongye Liang, Clarksville, MD (US); Scott Corey, Hydes, MD (US); Brian Bean, Baltimore, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 13/222,887

(22) Filed: Aug. 31, 2011

(65) Prior Publication Data

US 2012/0058460 A1    Mar. 8, 2012

Related U.S. Application Data

(60) Provisional application No. 61/378,558, filed on Aug. 31, 2010, provisional application No. 61/378,700, filed on Aug. 31, 2010.

(51) Int. Cl.
| | |
|---|---|
| *C12Q 1/68* | (2006.01) |
| *B01L 3/00* | (2006.01) |
| *G01N 33/58* | (2006.01) |
| *B01L 7/00* | (2006.01) |

(52) U.S. Cl.
CPC ...... *B01L 3/502784* (2013.01); *G01N 33/582* (2013.01); *B01L 7/52* (2013.01); *B01L 7/525* (2013.01); *B01L 2200/143* (2013.01); *B01L 2200/147* (2013.01); *B01L 2400/082* (2013.01); *Y10T 137/0318* (2015.04)

(58) Field of Classification Search
None
See application file for complete search history.

(56) References Cited

U.S. PATENT DOCUMENTS

| | | | |
|---|---|---|---|
| 6,197,510 B1 | 3/2001 | Wittwer et al. | |
| 6,379,929 B1 * | 4/2002 | Burns et al. | 435/91.2 |
| 9,709,559 B2 | 7/2017 | Benerjee et al. | |
| 2003/0224371 A1 * | 12/2003 | Thomas et al. | 435/6 |

(Continued)

FOREIGN PATENT DOCUMENTS

| | | |
|---|---|---|
| JP | 2003-507696 A | 2/2003 |
| JP | 2005-514618 A | 5/2005 |

(Continued)

OTHER PUBLICATIONS

PCT International Search Report and Written Opinion, issued in PCT/US2011/050038 dated Feb. 8, 2012, 24 pages.

(Continued)

*Primary Examiner* — Betty J Forman
(74) *Attorney, Agent, or Firm* — Rothwell, Figg, Ernst & Manbeck, P.C.

(57) ABSTRACT

The present invention, in one aspect, provides methods and systems for controlling slugs using temperature dependent fluorescent dyes. In some embodiments, the present invention uses one or more techniques to enhance the visibility of slugs, enhance a system's ability to differentiate between slugs, and enhance a system's ability to identify the positions of slugs.

30 Claims, 13 Drawing Sheets

(56) References Cited

U.S. PATENT DOCUMENTS

| | | | |
|---|---|---|---|
| 2007/0241068 A1* | 10/2007 | Pamula et al. | 210/806 |
| 2008/0003588 A1* | 1/2008 | Hasson et al. | 435/6 |
| 2008/0166793 A1* | 7/2008 | Beer et al. | 435/287.2 |
| 2008/0176289 A1 | 7/2008 | Zeng et al. | |
| 2009/0053726 A1 | 2/2009 | Owen et al. | |
| 2009/0054261 A1 | 2/2009 | Hughes et al. | |
| 2009/0203063 A1 | 8/2009 | Wheeler et al. | |
| 2010/0173394 A1* | 7/2010 | Colston et al. | 435/287.2 |
| 2010/0191482 A1 | 7/2010 | Hasson et al. | |
| 2011/0048547 A1 | 3/2011 | Hasson et al. | |
| 2011/0091877 A1 | 4/2011 | Murphy et al. | |

FOREIGN PATENT DOCUMENTS

| | | |
|---|---|---|
| WO | 2008/005248 A2 | 1/2008 |
| WO | 2009/021215 A1 | 2/2009 |
| WO | 2009/112594 A2 | 9/2009 |
| WO | 20101036352 A1 | 4/2010 |
| WO | 2010/085727 A1 | 7/2010 |

OTHER PUBLICATIONS

Coppeta et al., "Dual emission laser induced fluorescence for direct planar scalar behavior measurements," Experiments in Fluids, vol. 25, pp. 1-15 (1998).

Davis, "Microfluidics: its Impact on Drug Discovery," Innovations in Pharmaceutical Technology, pp. 24-27 (2008).

Glockner et al., "Thermocapillary control of microfluidic transport with a stationary cyclic heat source," J. Micromech. Microeng., vol. 15, pp. 2216-2229 (2005).

Hardt et al., "Development of a Slug-Flow PCR Chip with Minimum Heating Cycle Times," NSTI-Nanotech, vol. 1, pp. 55-58 (2004).

Horn et al., "Determining Optical Flow," Artificial Intelligence, vol. 17, pp. 185-203 (1981).

Liu et al., "Microfluidic device for robust generation of two-component liquid-in-air slugs with individually controlled composition," Microfluid Nanofluid, vol. 9, pp. 933-943 (2010).

Lucas, "Generalized Image Matching by the Method of Differences," Doctoral Dissertation, Computer Science Department, Carnegie-Mellon University, Pittsburgh, PA (1984).

Lucas, et al. "An Iterative Image Registration Technique with an Application to Stereo Vision," Proceedings of Imaging Understanding Workshop, pp. 674-679 (1981).

Reichert et al., "Micro Flow-Through Thermocycler with Simple Meandering Channel with Symmetric Temperature Zones for Disposable PCR-Devices in Microscope Slide Format," Journal of Bionic Engineering, vol. 5, No. 4, pp. 291-298 (2008) (abstract).

Tanthapanichakoon, et al., "Design of mixing in microfluidic liquid slugs based on a new dimensionless number for precise reaction and mixing operations," Chemical Engineering Science, vol. 61, pp. 4220-4232 (2006).

* cited by examiner

SLUG CONTROL DURING THERMAL CYCLING

CROSS-REFERENCE TO RELATED APPLICATIONS

This application claims the benefit of priority to U.S. Provisional Patent Application No. 61/378,558, filed on Aug. 31, 2010, the disclosure of which is incorporated herein by reference in its entirety. This application also claims the benefit of priority to U.S. Provisional Patent Application No. 61/378,700, filed on Aug. 31, 2010, the disclosure of which is incorporated herein by reference in its entirety.

BACKGROUND

1. Field of the Invention

The present invention relates to systems and methods for controlling the position of one or more slugs, droplets, plugs, boluses, etc. (hereinafter "slugs"). More particularly, aspects of the present invention relate to systems and methods for identifying and controlling the position of a slug in a microfluidic device.

2. Description of the Background

Devices for performing chemical, biological, or other reactions often feature one or more microfluidic channels having thermal control elements that are used to subject one or more reactants to a desired thermal profile. An example of such a device includes a microfluidic device for performing polymerase chain reaction (PCR) amplification of DNA molecules, or a microfluidic molecular diagnostic platform that performs PCR on a patient sample and then uses the PCR product for genotyping by performing a high resolution melt analysis. A description of PCR amplification, and an example of one possible microfluidic device including thermal control elements for PCR amplification and thermal melt analysis, are provided in U.S. patent application Ser. No. 12/165,043, which is hereby incorporated by reference.

In many applications of such devices, such as PCR amplification and thermal melt analysis, one or more fluorescent dyes are used to indicate various states of the reactants. For example, dyes such as the Alexa Fluor family of fluorescent dyes produced by Molecular Probes, the LCGreen dyes produced by Idaho Technology Inc., or SYBR Green can be used to monitor the temperature of reactants as well as other chemical properties.

Accurately controlling and monitoring the reactions, for example, by accurately placing the slugs of reactants in proximity to the thermal control elements and accurately reading the fluorescence of the slugs, may require determining the location of each slug, the boundaries between adjacent slugs, or other features of slugs within a channel. One method of facilitating the identification of individual sample slugs (i.e., slugs containing reactants) is to use a spacing or blanking slug with an alternative dye in between each sample slug. For example, the spacing or blanking slug may contain a first color dye (such as a red dye, e.g., Alexa Red or Alexa Fluor 647) while the samples contain an intercalating dye of a second color (such as an intercalating green dye, e.g., LCGreen or Sybr green). However, many dyes are known to have temperature dependent fluorescence. In some instances, the fluorescence of these dyes can change by a factor of two or more over the range of temperatures typically used for PCR amplification and thermal melt analysis. The dyes generally tend to lose their fluorescence intensity when heated, and gain fluorescent intensity when cooled.

Because the fluorescence of the dyes will increase when the slugs are cooled and decrease when the slugs are heated, slugs including temperature-dependent dyes may appear to move (for example, expanding and contracting) during thermal cycling. If real-time feedback (such as an imaging system using a signal intensity threshold approach) is desired for control of the flow of slugs through a microfluidic device, this apparent movement may interfere with a system's ability to perform fluid control (e.g., accurately placing the slugs in thermal contact with the thermal control elements) and to analyze the slugs.

Accordingly, what is desired are systems and methods for accurately and precisely controlling slugs during thermal cycling.

SUMMARY OF THE INVENTION

In one aspect, the present invention includes a method for controlling the position of a slug in a microfluidic device. In one embodiment, the method may include exciting a fluorescent dye in the slug, acquiring an image of the fluorescence of the slug, processing data from a region of interest in the image, identifying a position of the slug within the region of interest from the processed image data, and controlling the position of the slug based on the identified position of the slug.

In a further embodiment, the step of exciting a fluorescent dye in the slug may include exposing the slug to a light source of sufficient power such that the fluorescence of the dye will exceed a maximum intensity value of the image. In an alternate embodiment, the step of exciting a fluorescent dye in the slug may include modulating the output of an excitation source according to a measured state of the slug. In one embodiment, this measured state of the slug may be the temperature of the slug. In yet a further embodiment, modulating the output of an excitation source may include modulating the power input into the excitation source.

In an alternate embodiment, the step of exciting a fluorescent dye in the slug comprises exposing a region of the slug to a high intensity light source. In another alternate embodiment, the method may further include the step of photobleaching a portion of the slug. In this embodiment, the step of identifying the portion of the slug may include identifying the photobleached portion of the slug. In one embodiment, the dye is relatively insensitive to temperature change.

In a further embodiment of the method, the step of processing data in a region of interest in the image may include scaling intensity values in the region of interest such that the maximum intensity value in the region of interest is scaled to be the maximum intensity value for the image. In one further embodiment, the step of processing data in a region of interest in the image may include scaling intensity values in the region of interest according to a measured state of the slug. The measured state may be temperature in one further embodiment of the method.

In one embodiment, the step of identifying a position of the slug within a region of interest may include identifying pixels that satisfy threshold conditions in two or more wavelength planes of the image. The wavelength planes may be color planes in some embodiments.

In one embodiment, the step of identifying a position of the slug within the region of interest may include using information about the predicted thermal expansion of the slug to identify a position of the slug.

In one embodiment, the step of identifying a position of the slug within the region of interest may include cross-correlating the region of interest with a predetermined template image.

In one embodiment, the step of identifying a position of the slug within the region of interest may include identifying two or more points of the slug and averaging the positions of those two or more points.

In one embodiment, the step of controlling the position of the slug may include using a proportional-integral-derivative control device that derives the proportional, integral, and derivative control values from the identified position of the slug. Alternately, in one embodiment, the step of controlling the position of the slug may include modulating a control element, the control element being operatively engaged with the microfluidic device, based on an expected or measured state of the slug.

In another aspect, the invention includes a method for controlling the position of fluid slugs in a microfluidic device, which may include the steps of providing a first slug in the microfluidic device, wherein the first slug includes a first dye; providing a second slug in the microfluidic device, wherein the second slug includes a second dye; acquiring an image of a region of interest of a microfluidic device, wherein the region of interest may include one or more of the first and second slugs; processing data from a region of interest in the image; identifying a boundary between the first slug and the second slug within the region of interest from the processed image data; and controlling the position of the first slug and the second slug based on the identified boundary between the first and second slugs.

In one embodiment, one of the first slug or the second slug is a sample slug containing a biological sample to be processed and/or analyzed, and the other is a blanking slug containing no sample to be processed and/or analyzed. In another embodiment, the first dye is a fluorescent dye that fluoresces at a first wavelength of light, and the second dye is a fluorescent dye that fluoresces at a second wavelength of light. In one embodiment, the method may further include the step of exciting the first and second fluorescent dye in the first and second slugs.

In one embodiment of the method, the step of identifying a boundary between the first and second slug within the region of interest may include identifying pixels that satisfy threshold conditions in a first wavelength plane of the image and a second wavelength plane of the image. In another embodiment, the step of identifying a boundary between the first slug and the second slug within the region of interest comprises cross-correlating the region of interest with a predetermined template image.

In a further embodiment of any of the preceding embodiments, the slug may undergo changes in temperature.

One aspect of the invention may include a method for controlling the position of a slug in a microfluidic device. In one embodiment, this method may include the steps of acquiring an image of a slug in a microfluidic device, processing data from a region of interest in the image, identifying a position of the slug within the region of interest from the processed image data, and controlling the position of the slug based upon the identified position of the slug. In a further embodiment, the slug may include a fluorescent dye. In yet a further embodiment, the method may further include the step of exciting the fluorescent dye in the slug.

One aspect of the invention may include a system for controlling the position of a slug within a microfluidic device. The system may comprise: (a) a microfluidic device comprising one or more fluid channels and one or more slugs in the one or more fluid channels; (b) a slug excitation device configured to excite the one or more fluorescent dyes within the one or more slugs; (c) a light-sensing unit configured to capture light from at least a region of interest of the microfluidic device, wherein the region of interest includes one or more of the slugs; (d) a processing unit configured to receive information from the light-sensing unit; (e) a position identification unit configured to identify the position(s) of one or more of the slugs within the region of interest; and (f) a slug control unit, configured to position the one or more slugs within the microfluidic device based upon the identified position of the one or more slugs.

In one embodiment, the slug control unit may include a proportional-integral-derivative control unit operatively engaged with a fluid control device configured to move the slug. In another embodiment, the light-sensing unit may include a digital single-lens reflex camera.

In another embodiment, the one or more slugs include one or more fluorescent dyes, and the system may further include a slug excitation device configured to excite the one or more fluorescent dyes within the one or more slugs. In a further embodiment, the slug excitation device is a light source.

Another aspect of the invention may include a method for controlling the position of a sample slug in a microfluidic device which is surrounded by blanking slugs. In one embodiment, the method may comprise providing a first blanking slug including a fluorescent dye and a second blanking slug including a fluorescent dye, wherein said first and second blanking slugs surround the sample slug; exciting a fluorescent dye in the blanking slugs; acquiring an image of the blanking slugs and sample slug, wherein the image captures the fluorescence of the blanking slugs; processing data from a region of interest in the image; identifying a position of the sample slug within the region of interest from the processed image data; and controlling the position of the sample slug based on the identified position of the sample slug. In a further embodiment, the sample slug may contain little or no fluorescent dye. Alternately, the sample slug may contain a dye that fluoresces at a first wavelength, and the first and second sample slugs may each contain a dye that fluoresces at a second wavelength, and the first and second wavelength are different.

Another aspect of the invention may include a method for controlling the position of a sample slug in a microfluidic device, comprising providing a blanking slug comprising a fluorescent dye and a sample slug, wherein the blanking slug has an interface with the sample slug, exciting a fluorescent dye in the blanking slug; acquiring an image of at least a portion of the blanking slug and at least a portion of the sample slug; processing data from a region of interest in the image; identifying a position of the sample slug within the region of interest from the processed image data; and controlling the position of the sample slug based on the identified position of the sample slug.

In yet another aspect, the present invention includes a method for controlling the position of a slug during polymerase chain reaction (PCR) amplification, wherein the PCR has a denaturation step, an annealing step and an extension step, the method comprising exciting a fluorescent dye in the slug; acquiring images of the fluorescence of the slug; processing data in the images; identifying the position of the slug from the processed image data; and controlling the position of the slug based on the detected position, wherein the denaturation step is of shorter duration than the period at which the images are acquired.

In a further embodiment, the annealing step is of longer duration than the denaturation step, and at least a portion of the images are acquired during the annealing step. In a further embodiment, about 30% or more of the images are acquired during the annealing step. In yet a further embodiment, about 50% or more of the images are acquired during the annealing step.

In another further embodiment, the annealing step is about seven to about ten seconds in length. In another embodiment, the step of acquiring images of the fluorescence of said slug occurs at an image acquisition frequency greater than or equal to about one image per second. In a further embodiment, the image acquisition frequency is about one to about thirty images per second.

In a further embodiment, the extension step is of longer duration than the denaturation step, and at least a portion of the images are acquired during the extension step. In a one embodiment, about 30% or more of the images are acquired during the extension step. In yet another embodiment, about 50% or more of the images are acquired during the extension step. In yet a further embodiment, the extension step is about seven to about ten seconds in length. In one embodiment, the image acquisition frequency is greater than or equal to about one image per second. In another embodiment the image acquisition frequency may be about one to about thirty images per second.

In one embodiment, no images are acquired during the denaturation step. In another embodiment, the denaturation step has a duration of about one second, the annealing step has a duration of about eight seconds, and the extension step has a duration of about one second.

Another aspect of the invention includes a method for controlling the position of a slug during a polymerase chain reaction thermal cycle, wherein the method may comprise: a denaturation step comprising subjecting the slug to a temperature sufficiently high to allow denaturation; an annealing/extension step comprising subjecting the slug to a temperature lower than the denaturation temperature and which is sufficient to allow primer annealing and extension; exciting a fluorescent dye in the slug during the thermal cycle; acquiring images of the fluorescence of the slug; processing data in the images; identifying the position of the slug from the processed image data; and controlling the position of the slug based on the detected position.

In a further embodiment, the denaturation step comprises subjecting the slug to a first temperature sufficiently high to allow denaturation and a second temperature lower than the first temperature but still sufficiently high to allow denaturation during subsequent denaturing steps during the PCR thermal cycle. In yet a further embodiment, the first temperature is about 95° C. or greater, and wherein the second temperature is about 90° C. or lower.

In another aspect, the present invention includes a system for controlling the position of a slug within a microfluidic device. In one embodiment, the system may include the following: (a) a microfluidic device comprising one or more fluid channels, one or more thermal elements in communication with said one or more channels, and one or more slugs in the one or more fluid channels, wherein the one or more slugs include one or more fluorescent dyes, (b) a slug excitation device configured to excite the one or more fluorescent dyes within the one or more slugs; (c) a light-sensing unit configured to capture fluorescence at an acquisition rate from at least a region of interest of the microfluidic device, wherein said region of interest includes one or more of said slugs; (d) a temperature control unit configured to control the temperature of said slugs using said thermal elements of the microfluidic device; (e) a processing unit configured to receive information from said light-sensing unit; (f) a position identification unit configured to identify the position of one of said one or more slugs within said region of interest; and (g) a slug control unit, configured to position the slug within the microfluidic device based upon the identified position.

In one further aspect of the system, the temperature control unit is configured to subject said slug to a denaturation step at a first temperature for a first duration of time, an annealing step at a second temperature for a second duration of time, and an extension step at a third temperature for a third duration of time.

In one embodiment, the duration of the denaturation step is shorter duration than the period between image acquisitions. In one embodiment, the duration of the annealing step is longer than the duration of the denaturation step. and at least a portion of the images are acquired during the annealing step. Alternately, in another embodiment, the duration of the extension step is longer than the duration of the denaturation step, and at least a portion of the images are acquired during the extension step.

In one embodiment, the denaturation step has a duration of about one second, the annealing step has a duration of about eight seconds, and the extension step has a duration of about one second. In another embodiment, the denaturation step has a duration of about 2 seconds, the annealing step has a duration of about 1.5 seconds, and the extension step has a duration of about 6.5 seconds.

In another embodiment of the system, the temperature control unit is configured to subject the slug to a denaturation step at a first temperature for a first duration of time, and an annealing/extension step at a second temperature for a second duration of time.

In another embodiment, a method for controlling the position of a fluid slug during a polymerase chain reaction (PCR) amplification is provided, wherein the PCR comprises: a first denaturation step comprising subjecting the slug to a temperature sufficiently high to allow denaturation, and a second annealing and extension step comprising subjecting the slug to a temperature lower than the denaturation temperature to allow primer annealing and extension. The method may further comprise exciting a fluorescent dye in said slug; acquiring images of the fluorescence of said slug; processing data in said images; identifying the position of said slug; and controlling the position of said slug based on the detected position. In one embodiment of this method, no images are obtained during the denaturation step.

The above and other aspects and features of the present invention, as well as the structure and application of various embodiments of the present invention, are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF THE PREFERRED EMBODIMENTS

In one aspect, the present invention provides a system and method for controlling slugs that may include temperature-dependent fluorescent dye(s) during thermal cycling. In certain non-limiting embodiments, the present invention includes processes and systems for enhancing the ability of a system to determine the position of a slug within a microfluidic channel.

Figure 1:
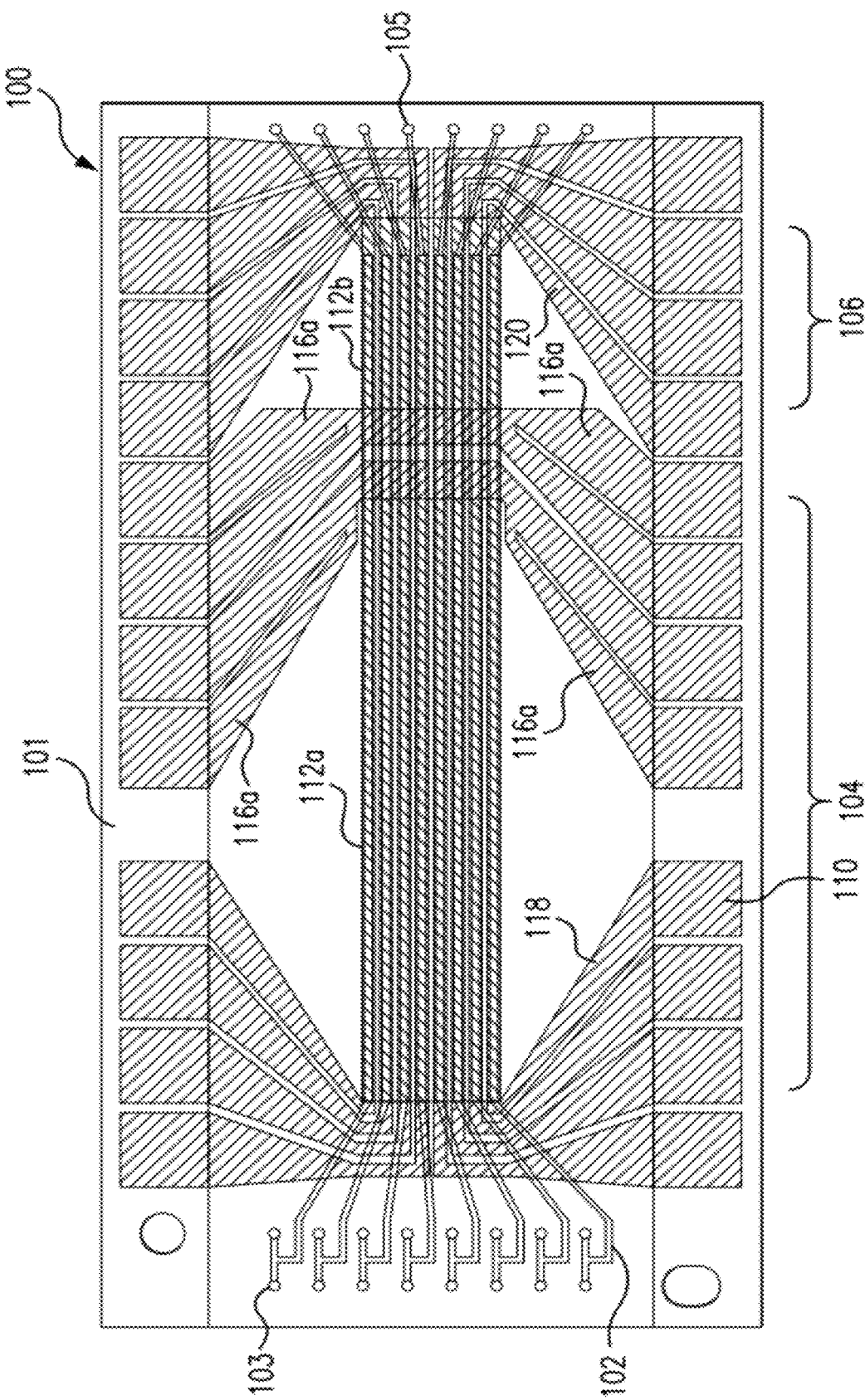
FIG. 1 illustrates a microfluidic device that can be used in conjunction with aspects of the present invention.

FIG. 1 illustrates a microfluidic device 100 that may be useful in performing aspects of the present invention. It will be appreciated by those of skill in the art that other devices (including other microfluidic devices) may be used in accordance with the present invention. In the illustrative embodiment, the microfluidic device 100 includes several microfluidic channels 102 extending across a substrate 101. Each channel 102 includes one or more inlet ports 103 (the illustrated embodiment shows two inlet ports 103 per channel 102) and one or more outlet ports 105 (the illustrated embodiment shows one outlet port 105 per channel 102). In exemplary embodiments of the device, each channel may be subdivided into a first portion extending through a PCR thermal zone 104 (as described below) and a second portion extending through a thermal melt zone 106 (as described below).

In an embodiment, the microfluidic device 100 further includes thermal control elements in the form of thin film resistive heaters 112 associated with the microfluidic channels 102. In one non-limiting embodiment, the thin film resistive heaters 112 may be platinum resistive heaters whose resistances are measured in order to control their respective temperatures. In the embodiment illustrated in FIG. 1, each heater element 112 comprises two heater sections: a PCR heater 112a section in the PCR zone 104, and a thermal melt heater section 112b in the thermal melt zone 106.

In one embodiment, the microfluidic device 100 may include a plurality of heater electrodes 110 connected to the various thin-film heaters 112a and 112b. In non-limiting embodiments, heater electrodes 110 may include PCR section leads 118, one or more PCR section common lead 116a, thermal melt section leads 120, and one or more thermal melt section common lead 116b. According to one embodiment of the present invention, a separate PCR section lead 118 is connected to each of the thin-film PCR heaters 112a, and a separate thermal melt section lead 120 is connected to each of the thin-film thermal melt heaters 112b.

Figure 2:
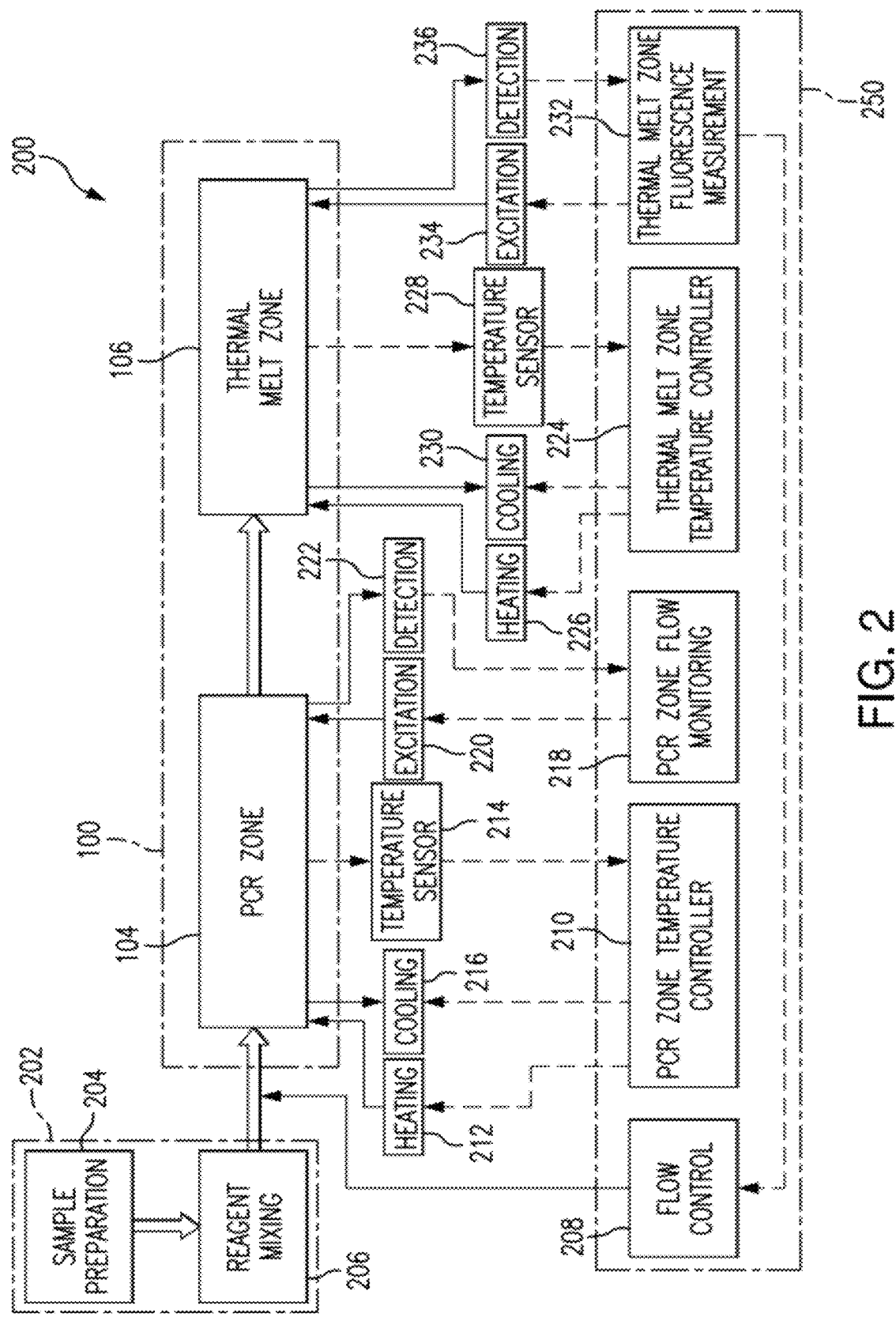
FIG. 2 is a functional block diagram of a system for using a microfluidic device that can be used in conjunction with aspects of the present invention.

FIG. 2 illustrates a functional block diagram of an exemplary system 200 for using a microfluidic device, such as microfluidic device 100. Again, it will be appreciated that the methods of the present invention are useful in conjunction with other alternative systems, including any devices and systems in which discrete samples are to be thermally cycled or otherwise thermally manipulated for processing and analysis. The DNA sample may be input in the microfluidic device 100 from a preparation stage 202. The preparation stage 202 may comprise appropriate devices for preparing the sample 204 and for adding one or more reagents 206 to the sample. Once the sample is input into the microfluidic device 100, e.g., at an input port 103, it flows through a channel 102 into the PCR zone 104 where PCR takes place. That is, as explained in more detail below, as the sample flows within a channel 102 through the PCR zone 104, it is exposed to the PCR temperature cycle a plurality of times to effect PCR amplification. Next, the sample flows into the thermal melt zone 106 where a high resolution thermal melt process occurs. Flow of sample into the microfluidic device 100 can be controlled by a flow controller 208. A control system 250 may comprise a flow controller 208, a PCR zone temperature controller 210, a PCR flow monitor 218, a thermal melt zone temperature controller 224, and a melt zone fluorescence measurement system 232. Alternatively, the control system may also comprise a flow controller 208, a PCR zone temperature controller 210, a thermal melt zone flow monitor, a thermal melt zone temperature controller 224, and/or a thermal melt zone fluorescence measurement system. PCR and thermal melt flow control modes may be combined or used in an alternating fashion.

The temperature in the PCR zone 104 can be controlled by the PCR zone temperature controller 210. The PCR zone temperature controller 210, which may be a programmed computer or other microprocessor or analog temperature controller, sends signals to the heater device 212 (e.g., a PCR heater 112a) based on the temperature determined by a temperature sensor 214 (such as, for example, an RTD or thin-film thermistor, or a thin-film thermocouple thermometer). In this way, the temperature of the PCR zone 104 can be maintained at the desired level or cycled through a defined sequence. According to some embodiments of the present invention, the PCR zone 104 may also be cooled by a cooling device 216 (for example, to quickly bring the channel temperature from 92° C. down to 55° C.), which may also be controlled by the PCR zone temperature controller 210. In one embodiment, the cooling device 216 could be a peltier device, heat sink or forced convection air cooled device, for example.

The flow of sample through the microfluidic channels 102 can be measured by a PCR zone flow monitoring system 218. In one embodiment, the flow monitoring system can be a fluorescent dye imaging and tracking system illustrated in U.S. patent application Ser. No. 11/505,358, incorporated herein by reference. According to one embodiment, the channels in the PCR zone can be excited by an excitation device 220 and light fluoresced from the sample can be detected by a detection device 222. An example of one possible excitation device and detection device forming part of an imaging system is illustrated in U.S. patent application Ser. Nos. 11/606,006 and 11/505,358, the entire disclosures of which are incorporated herein by reference.

The thermal melt zone temperature controller 224, e.g., a programmed computer or other microprocessor or analog temperature controller, can be used to control the temperature of the thermal melt zone 106. As with the PCR zone temperature controller 210, the thermal melt zone temperature controller 224 sends signals to the heating component 226 (e.g., a thermal melt heater 112*b*) based on the temperature measured by a temperature sensor 228 which can be, for example, an RTD, thin-film thermistor, or thin-film thermocouple. Additionally, the thermal melt zone 106 may be independently cooled by cooling device 230. The fluorescent signature of the sample can be measured by the thermal melt zone fluorescence measurement system 232. The fluorescence measurement system 232 excites the sample with an excitation device 234, and the fluorescence of the sample can be detected by a detection device 236. An example of one possible fluorescence measurement system is illustrated in U.S. patent application Ser. Nos. 11/606,006 and 11/505,358, the entire disclosures of which are incorporated herein by reference.

In accordance with aspects of the present invention, the thin film heaters 112 may function as both heaters and temperature detectors. Thus, in one embodiment of the present invention, the functionality of heating elements 212 and 226 and temperature sensors 214 and 228 can be accomplished by the thin film heaters 112.

In one embodiment, the system 200 sends power to the thin-film heaters 112*a* and/or 112*b*, thereby causing them to heat up, based on a control signal sent by the PCR zone temperature controller 210 or the thermal melt zone temperature controller 224. The control signal can be, for example, a pulse width modulation (PWM) control signal. An advantage of using a PWM signal to control the heaters 212 is that with a PWM control signal, the same voltage applied across the heaters may be used for all of the various temperatures required. In another aspect, the control signal could utilize amplitude modulation or alternating current. It is advantageous to use a control signal that is amplitude modulated to control the heaters 212 because a continuous modest change in voltage, rather than large voltage steps, avoids slew rate limits and improves settling time. Further discussion of amplitude modulation can be found in U.S. patent application Ser. No. 12/825,476, filed Jun. 29, 2010, which is incorporated herein by reference.

In some embodiments, the desired temperature for the heaters is reached by changing the duty cycle of the control signal. In one non-limiting example, the duty cycle of the control signal for achieving 95° C. in a PCR heater might be about 50%, the duty cycle of the control signal for achieving 72° C. in a PCR heater might be about 25%, and the duty cycle of the control signal for achieving 55° C. in a PCR heater might be about 10%. In other embodiments, other duty cycles can be used as would be apparent to persons skilled in the art.

The microfluidic device 100 and the system 200 can be used in conjunction with each other. Further, the microfluidic device 100 and the system 200 may be used in conjunction with the methods of the present invention. For example, one can use the microfluidic device 100 in connection with the flow controller 208, temperature controllers 210 and 224, and the excitation and detection devices 220, 222, 234, and 236 described above to identify and control the position of slugs that include temperature dependent fluorescent dye moving through the microfluidic channels 102 during thermal cycling, in accordance with aspects of the invention.

Figure 3A:
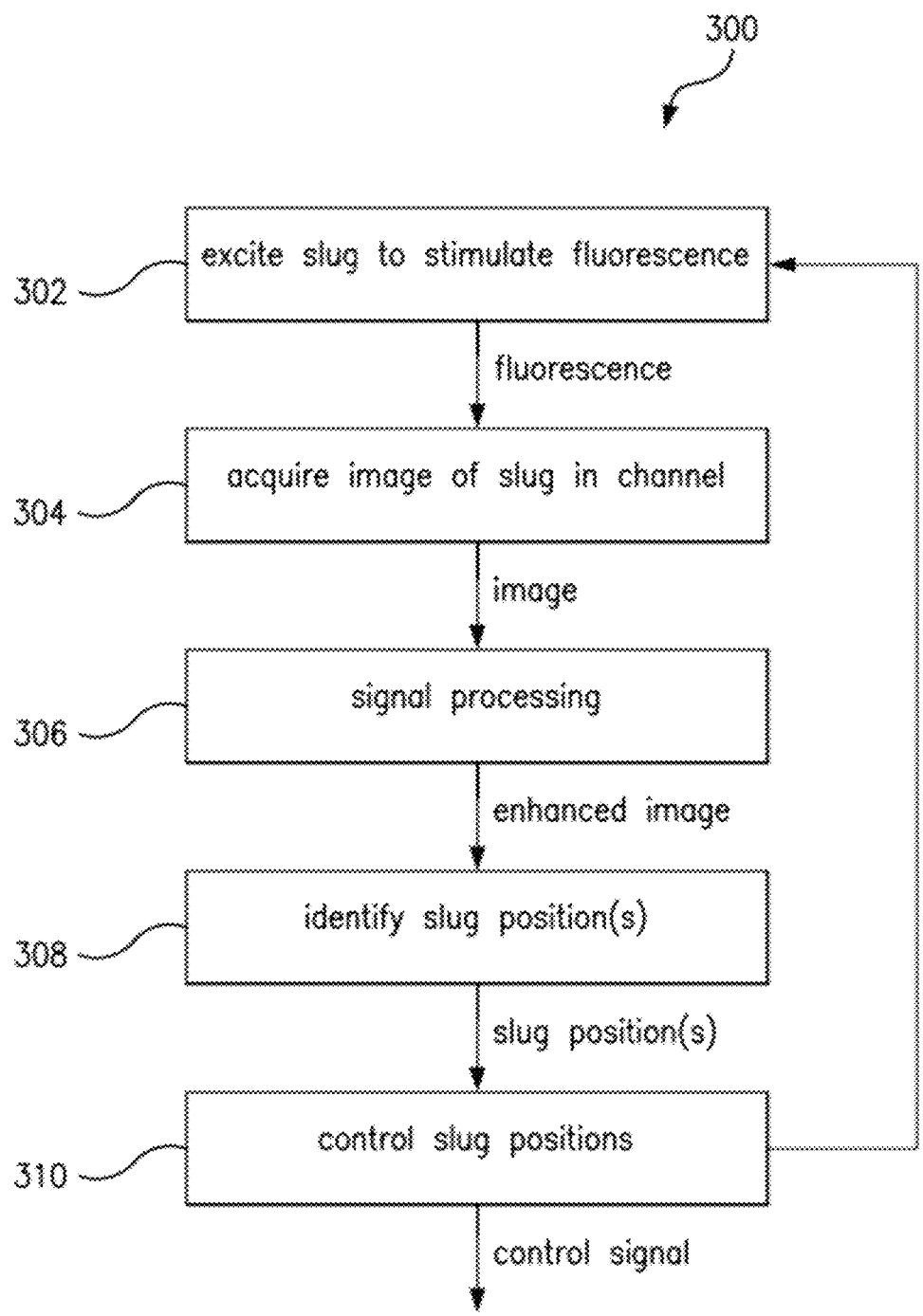
FIG. 3A illustrates a process for controlling one or more slugs in accordance with embodiments of the invention.

In non-limiting embodiments of the present invention, the position of slugs within a channel can be determined by analyzing regions of interest (ROIs) along the channel. In some embodiments, such analysis may include image analysis of the regions of interest. FIG. 3A illustrates a process 300 for controlling one or more slugs moving through a channel during thermal cycling in accordance with an embodiment of the present invention. In some embodiments, one or more slugs can include a fluorescent dye. The fluorescent dye may be temperature dependent in some embodiments.

As illustrated in FIG. 3A, the process 300 may begin at step 302 at which the slug is caused to fluoresce. The slug may be caused to fluoresce by a slug excitation light source, which may be any light source that is suitable for exciting fluorescence in a fluorescent dye, e.g. excitation with a light source of sufficient intensity, including lasers, LEDs, and certain lamps. For example, in some embodiments, the light source may include the excitation device 220 or the excitation device 234 stimulating the slug within a microfluidic channel 102 by emitting a predetermined wavelength or range of wavelengths of light or other radiation.

In some embodiments, step 302 may include a saturation approach. In the saturation approach, the intensity of the blanking slugs' fluorescence may be maximized, for example, by increasing the intensity of the blanking slug excitation light source (e.g., in some embodiments, increasing the output of the excitation device 220 or the excitation device 234). The intensity of the blanking slugs may also, or alternatively, be increased by increasing the concentration of dye within the blanking slugs. The saturation approach makes the blanking slugs fluoresce so brightly that they saturate the sensor despite variations in fluorescence that may occur, for example, due to temperature or other changes.

In one non-limiting example, a sensor may be used to detect the fluorescence of the slug. In some embodiments, the sensor may be detector device 222 or 226. In one embodiment, the sensor may include an 8-bit system (i.e., sensed values can range between 0 and 255). Examples of such sensors include any CCD, CMOS, or other appropriate camera that outputs an 8-bit image (e.g., a JPEG file format image). An example of such a sensor is described application U.S. Patent Application No. 61/378,471, entitled "Optical System for High Resolution Thermal Melt Detection," and U.S. Application Ser. No. 13/222,487 claiming priority therefrom, the entire disclosure of which is incorporated herein by reference. In an embodiment including an 8-bit sensor, the blanking slug intensity can be increased so that its fluorescence is sensed at the $255^{th}$ level for the highest expected temperature of the reaction. At lower temperatures, the fluorescence of the blanking slug will exceed the $255^{th}$ level of the sensor, but the sensor will still produce output at the $255^{th}$ level (i.e., the sensor will be "saturated").

Figure 4A:
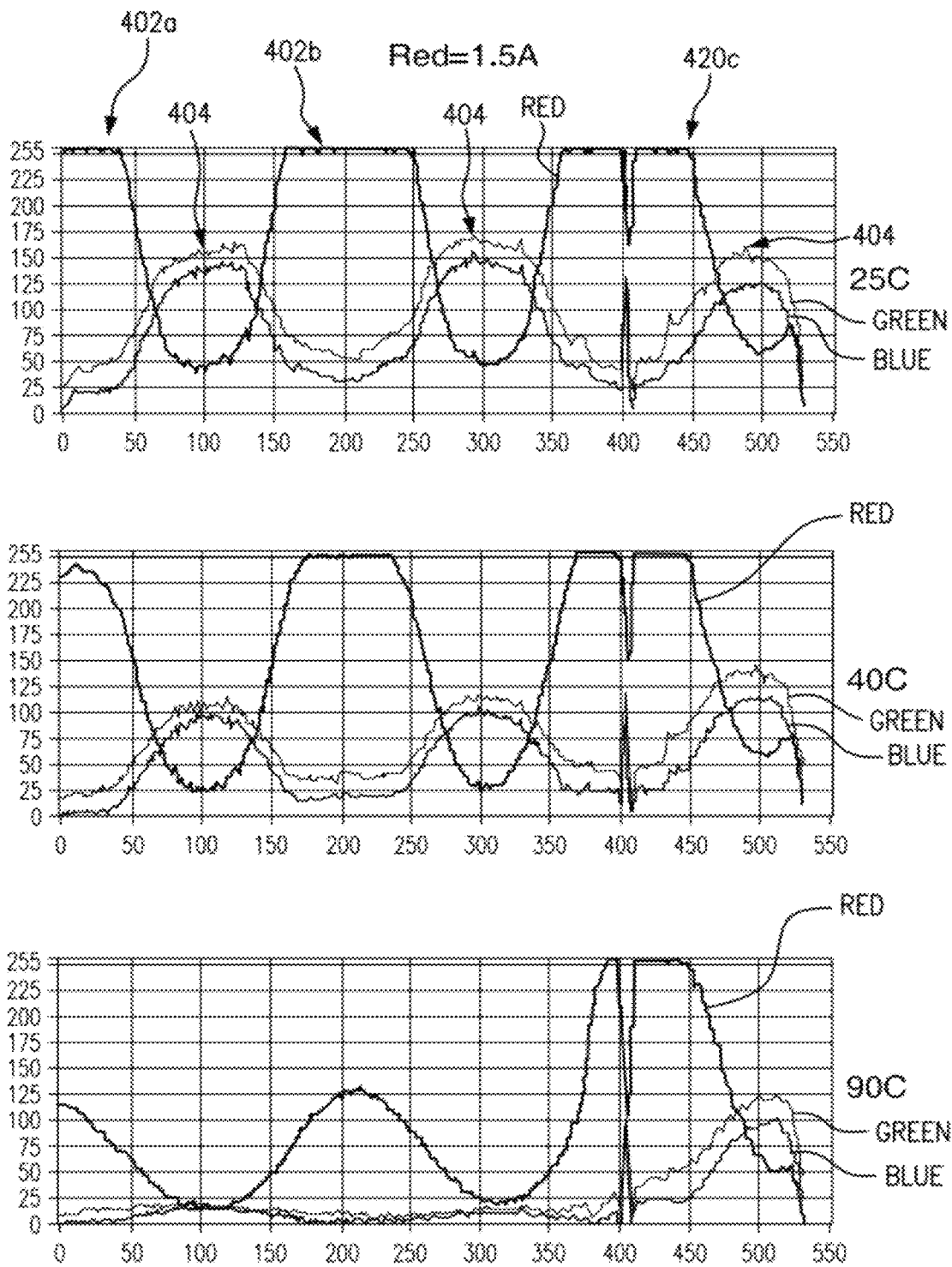
FIGS. 4A-B illustrates intensity profiles slugs in a microchannel in accordance with an embodiment of the invention.
Figure 4B:
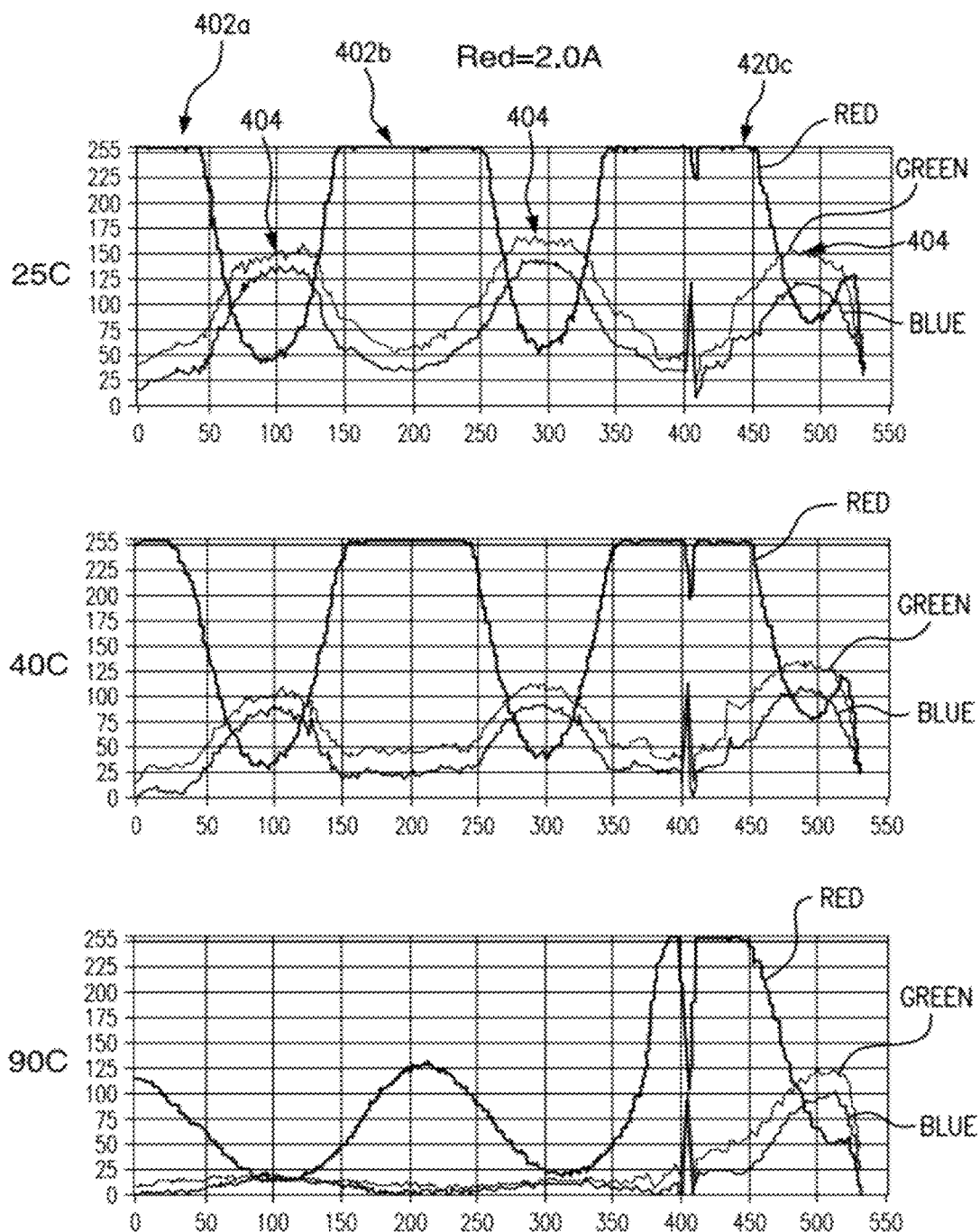

FIGS. 4A-B illustrate intensity profiles for a non-limiting example of red blanking slugs 402*a*, 402*b*, and 402*c* and blue/green sample slugs 404 under different temperature conditions (i.e., at 25° C., 40° C., and 90° C. as shown in FIGS. 4A-B). The plots in FIG. 4A are for a lower LED current (i.e., a lower excitation power) than those in FIG. 4B. In this example, the saturation approach has been used so that the fluorescence of the red dye saturates the sensor at 25° C. and 40° C. Thus, FIGS. 4A-B illustrate that the saturation approach may be used in some embodiments where full saturation is only at some temperatures less than the full range of expected temperatures for the reaction (that is, in the non-limiting example of FIGS. 4A-B, full saturation of the sensor only occurs at 25° C. and 40° C.). While full saturation is not required at each temperature, it is preferable in some embodiments that the intensity of the fluorescence is increased enough to ensure that blanking slugs 402a-c can be readily distinguished from sample slugs 404.

Figure 5:
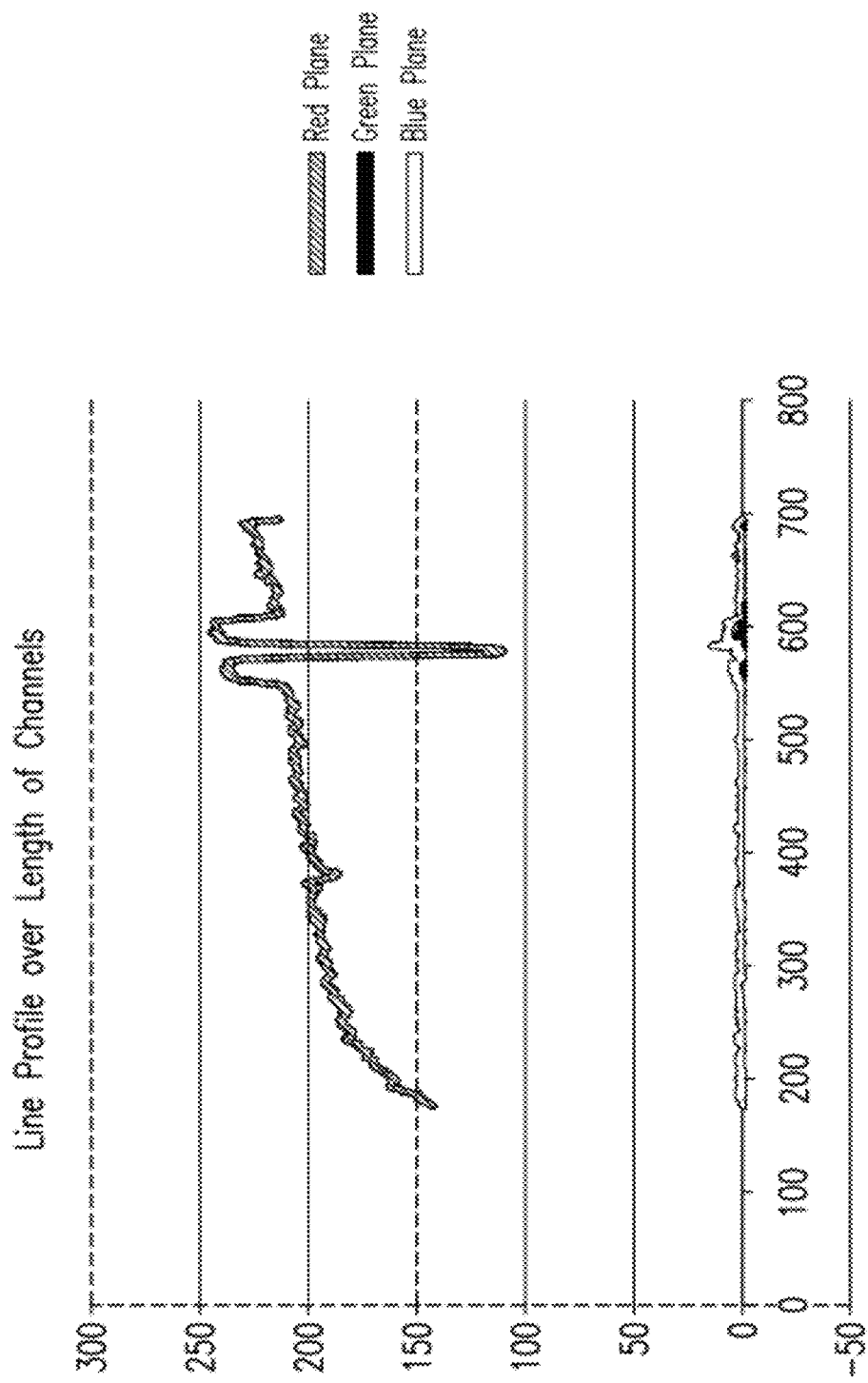
FIG. 5 is an intensity profile for a dye-filled microchannel that is exemplary of some embodiments of the invention.

FIGS. 4A-B also illustrate that the rightmost slug 402c represented in each plot is not uniformly heated and thus its intensity profile is not uniform. In some embodiments, this may be caused by a space between two thermal control elements (e.g., a space between a PCR heater 112a and a thermal melt heater 112b along a microfluidic channel 102 in the microfluidic device 100). FIG. 5 illustrates an intensity profile for a non-limiting example of a fluid including a red dye filling the entire channel (e.g., red dye filling the entire microchannel 102 without any sample slugs), showing a non-uniform fluorescence across the channel. In such an embodiment, the reference profile, such as the one illustrated in FIG. 5, can be used to normalize slug intensity profiles, such as the intensity profiles shown in FIGS. 4A-B. Normalization techniques may be based on division or subtraction of the reference profile, for example. In one specific example, the reference profile (such as that shown in FIG. 5) shows that intensities are greater on the right side indicating greater excitation light. Dividing the slug profile (e.g., those shown in FIGS. 4A-B) by the reference profile (e.g., that of FIG. 5) corrects any scaling error caused by non-uniform excitation light. It will be apparent to one skilled in the art that such a normalization could correct for detector non-uniformity as well (e.g., vignettes).

In another non-limiting embodiment, the temperature dependence of the fluorescent dyes may be overcome by modulating the intensity of the excitation light used in step 302 (i.e., "light modulation"). For instance, if the red blanking slug is excited by a laser or LED, the power of output of the excitation source can be increased or decreased (e.g., by adjusting the current and/or voltage) as necessary to maintain an approximately constant fluorescence intensity despite variations in temperature of the sample or blanking slug. For example, in a non-limiting embodiment, the fluorescence of the dye can decrease as the temperature of the reaction increases. To compensate for this, the power output of the excitation source can be appropriately increased as the temperature of the reaction increases to maintain an approximately constant fluorescence intensity.

Light modulation can be implemented in a variety of ways in accordance with aspects of the invention. For example, in some embodiments, software determines the temperature of the dye (e.g., the PCR zone temperature controller 210 or the thermal melt zone temperature controller 224 knows the temperature of the corresponding zone and thus can determine the temperature of the dye). In a non-limiting embodiment, the light power is varied by using an analog output on a data acquisition card, of which National Instruments PXI-6289 and Measurement Computing PCI-2517 are two non-limiting examples. In another embodiment, an excitation laser or LED can be modulated using hardware feedback. For example, if a circuit is used to measure the temperature of a sensor on a microfluidic device (e.g., a resistance temperature detector whose voltage and current are measured), then signals from that circuit can be used as inputs to vary the light source (e.g., LED or laser) power as appropriate. The variation of the light source power can be calculated by using an intensity profile for the dye, such as the intensity profile shown in FIG. 12. Light modulation can be achieved by using an appropriate feedback mechanism. One possible feedback mechanism is to measure the current through an RTD as a measure of slug temperature. An appropriately transformed version (scaled, inverted, offset, etc.) of the current can be used to drive a constant current sourced LED. In one specific non-limiting example, as the RTD increases in temperature its current decreases (assuming a positive temperature coefficient of resistance). Therefore, an inverted measure of RTD current could be used to drive the LED (i.e., driving the LED with more current to provide more light to compensate for a fluorescence that decreases as temperature of the dye increases). In yet another embodiment, the excitation source can be turned on and off at different duty cycles (i.e., pulse width modulated) to maintain an approximately constant fluorescence intensity during varying temperatures. For example, if intensity drops by two-fold for a given increase in temperature, then the duty cycle to be used could be doubled.

In another non-limiting embodiment, a laser or other appropriately imaged and focused excitation source can be used to create an excitation stripe across a plurality of microchannels so that the slugs fluoresce brightly in the area of the excitation stripe. In an embodiment, the excitation stripe may be placed in a small area of nominally constant temperature (e.g. a region that is not subject to thermal cycling) so that the fluorescence of slugs in the excitation stripe will not vary and the slugs could remain under control despite temperature variation in other areas of the channel. In some embodiments, the focused excitation could also be used to saturate the imaging system as described above.

In another embodiment, a laser (or other appropriately imaged and focused light source) can be used to photobleach a spot or stripe into the dye. By destroying the fluorophore in a slug through exposure to the focused light source (e.g., the laser), one can create a "dark" spot that can be tracked within the channel. In this manner, the photobleached spot or stripe can be tracked and used to identify the position of the slug since the fluorescence of the dark spot will not vary. In one embodiment, the edges of the photobleached spot or stripe are sharper than the edges of the diffused slugs, which may aid in using the photobleached spot or stripe to control the positions of the slugs. In one embodiment, the center of the photobleached spot or stripe may be tracked, since the dark, photobleached region does not exhibit temperature-dependent fluorescence.

In one non-limiting embodiment, the PCR cycle is adjusted so that the denaturation step is very short. In a microfluidic device, typical PCR thermal cycling times through the denaturation/annealing/extension steps can include, for example, 5 s/5 s/5 s or 10 s/10 s/10 s. However, the denaturation step only needs to be long enough for the double stranded DNA to separate into single strands. Thus, in one non-limiting example, the denaturation step may last only about 3 seconds or less, preferably about 2 seconds or less, and more preferably about 1 second or less.

PCR thermal cycling times are traditionally specified using the hold (i.e., dwell) times, and generally do not include transition time. In one embodiment of the present invention, the temperature-induced intensity variation may be minimized by limiting (in some embodiments) and/or extending (in other embodiments) transition and/or dwell times. Both the transition and dwell times for denaturation could be limited, for example. In embodiments, the denaturation step could have a very short duration, and momentary denaturation may be sufficient in some embodiments. In addition to momentary, specific, non-limiting examples of denaturation durations may include about 3 seconds, 2 seconds, 1 second, 0.5 seconds, and 0.25 seconds.

In one embodiment, the denaturation period may be shorter than the frequency at which the flow monitoring system is updated or acquires images of the slugs in the microfluidic channel 102 (e.g., once per second). By making the denaturation step relatively short, few if any images acquired for flow monitoring will be obtained at the extreme temperatures (with their corresponding extreme intensity variation) used in denaturation step. In an aspect of the invention, this may be accomplished with a microfluidic device, as heat is rapidly transmitted from heating elements to the DNA sample. In one embodiment, the microfluidic device 100 is ideally suited for this purpose because the embedded heaters 112 are capable of rapid heating.

To ensure that no flow control images are acquired during denaturation, which may be preferred in some embodiments, the image acquisition period of the flow monitoring system may be longer than the period of the denaturation step. In a further embodiment, the flow monitoring process and/or the image acquisition process will be synchronized with the thermal cycle to avoid capturing images of the slugs during the denaturation step of a PCR thermal cycle.

In another non-limiting embodiment, the annealing step may be lengthened so that the flow monitoring system is updated while a slug is holding at the annealing temperature. For example, in one non-limiting embodiment, the annealing step may be extended to about 3 to about 60 seconds. More preferably, the annealing step is about 5 to about 15 seconds. More preferably, the annealing step is about 5 to about 10 seconds. This serves a dual purpose: first, it provides sufficient time for primers to attach; second, it allows the flow control system to operate primarily on images that are collected at a temperature that varies minimally (and thus varies the fluorescence of the slugs varies minimally). In one embodiment, the lengthened annealing step will be long relative to the period between updates of the flow monitoring system or between acquisition of images. In a further embodiment, the annealing step may be sufficiently long to ensure that the majority of the images used for flow control are acquired during the annealing step. In one embodiment, the flow monitoring system may acquire images (and therefore be updated) at a rate of about 1 or about 5 or about 10 or about 15 or about 20 or about 25 or about 30 or more images/second. An annealing step of about 5 to about 10 seconds in duration would allow for the acquisition of about 5 to about 300 images during the annealing step for use in flow monitoring.

In another non-limiting embodiment, the extension step may be lengthened so that the flow monitoring system is updated while holding the extension temperature. For example, in one non-limiting embodiment, the extension step may be extended to about 3 to about 60 seconds. More preferably, the extension step is about 5 to about 15 seconds. More preferably, the extension step is about 5 to about 10 seconds. This serves a dual purpose: first, it provides sufficient time for the polymerase to extend; second, it allows the flow control system to operate primarily on images that are collected at a temperature that varies minimally (and thus varies the fluorescence of the slugs minimally) which images therefore have constant intensity. In one embodiment, the lengthened extension step will be long relative to the period between updates of the flow monitoring system, or between acquisition of images. In an embodiment, the extension step may be sufficiently long to ensure that the majority of the images used for flow control are acquired during the extension step. In one embodiment, the flow monitoring system may obtain images (and therefore be updated) at a rate of about 1 or about 5 or about 10 or about 15 or about 20 or about 25 or about 30 or more images/second. An extension step of about 5 to about 10 seconds in duration would allow for the acquisition of about 5 to about 300 images during the extension step for use in flow monitoring.

In yet another non-limiting embodiment, the majority of the images used in controlling the position of a fluid slug during PCR may be obtained during the annealing and/or extension steps. In one embodiment, about 30% or more of the images used in controlling the position of a fluid slug during a PCR thermal cycle are obtained during the annealing and/or extension steps. In a further embodiment, about 35% or about 40% or about 45% or about 50% or more of the images used in controlling the position of the fluid slug are obtained during the annealing and/or extension steps.

A preferred and non-limiting embodiment of a PCR thermal cycle useful in the present invention is an about 1 second/8 seconds/1 second denature/anneal/extension PCR cycle, where the times are the total length of time allotted to each step (regardless of transition time). In this embodiment, the annealing step is much longer than the other two steps, which allows most of the images acquired for flow control to be acquired at the annealing temperature. This results in the fluorescence intensity of the slugs being roughly constant (i.e., not varying significantly with temperature) during image acquisition.

In one embodiment of the invention, the flow monitoring system can be programmed such that no images are acquired while the PCR thermal cycle is in one or more of the denaturing, annealing or extensions phases.

In another embodiment, a two step PCR thermal cycle can be used to effectuate PCR while maintaining slug control under thermal cycling. In a first step, the sample may be subjected to a high temperature for denaturation. In a second step, the sample may be subjected to a lower temperature for primer annealing and extension. In one embodiment, the denaturation step may be short relative to the annealing/extension step. The two-step PCR offers the advantage that the control system must only contend with two different intensities (due to the temperatures at the two different steps) rather than three, as would be typical with a traditional PCR thermal cycle profile.

Thus, in one embodiment, there is provided a method for controlling the position of a fluid slug during a two-step PCR reaction, wherein the PCR comprises a first denaturation step comprising subjecting the slug to a temperature sufficiently high to allow denaturation, and a second annealing and extension step comprising subjecting the slug to a temperature lower than the denaturation temperature to allow primer annealing and extension, wherein the method comprises (a) exciting a fluorescent dye in said slug; (b) acquiring images of the fluorescence of said slug; (c) processing data in said images; (d) identifying the position of said slug; and (e) controlling the position of said slug based on the detected position.

Similarly, as an alternative to or in conjunction with the above methods, the temperatures of the denaturation/annealing/extension steps can be modified to improve slug control by reducing intensity variation. In this approach, the temperatures of the various PCR thermal cycle steps are adjusted to be more similar, thus reducing intensity variation between the steps due to the temperature dependence of fluorescence. Naturally, there are biological and thermodynamic limits to these approaches, as will be readily understood by one of skill in the art.

One non-limiting example of adjusting the PCR thermal cycle step temperatures is to lower the denaturation temperature. Conventionally, the denaturation temperature is set higher than thermodynamically required (e.g., at 95° C.) in order to ensure all of the nucleic acid molecules are denatured. However, this may result in reduced slug control because the range of fluorescence intensities is increased when the denaturation temperature is increased. In one embodiment, to reduce variation in intensity and improve slug control, the denaturation temperature can be reduced. In one non-limiting embodiment, the denaturation temperature may be reduced to 90° C. or less. The precise denaturation temperature required is assay dependent and may be determined by routine experiment (or theoretical calculation) as will be obvious to those skilled in the art. In another aspect, the sample may be "hot-started" with one period of high temperature (e.g., 95° C.) to separate long nucleic acid strands (such as human genomic DNA) before proceeding with PCR cycling using a second, lower denaturation temperature (e.g., 90° C.). In one embodiment, a "hot start" may be applied for about 30 to about 60 seconds, and may be applied before the samples are formed into discrete slugs. Alternately, the "hot start" may be applied after the samples are formed into slugs. Using such a "hot start" after the slugs are formed does not result in problems for image control, as the temperature is constant and not rapidly changing. The lower denaturation temperature may have a very short duration in some embodiments. In some embodiments, momentary denaturation may be sufficient. In other embodiments, specific non-limiting examples of denaturation durations may include about 3 seconds, about 2 seconds, about 1 seconds, about 0.5 seconds, and about 0.25 seconds.

In other non-limiting embodiments, the annealing and extension temperatures may also be modified to result in less intensity variation (within biological and thermodynamic limits). One of skill in the art will readily understand the limitations of such modification, and will be able to do so with only routine experimentation or calculation. Adjusting the annealing/extension temperature may allow the generation of results that are similar to the two-step PCR process described above. For example, in one embodiment, the annealing temperature (which is often the lowest of the three temperatures used in PCR processes) may be raised to be closer to the extension temperature. This will allow more slug control images to be collected at similar temperatures, which reduces intensity variation due to temperature. In an alternate embodiment, the extension temperature could be reduced to be closer to the annealing temperature. The duration of the annealing and/or extension steps may have to be modified (e.g. lengthened) to account for lower activity, or lower specificity, at "non-ideal" temperatures as will be obvious to one skilled in the art. For example, a typical PCR protocol of 95/55/72° C. could be adjusted to have a higher anneal (95/60/72° C.) or a lower extension temperature (95/55/60° C.).

Figure 6:
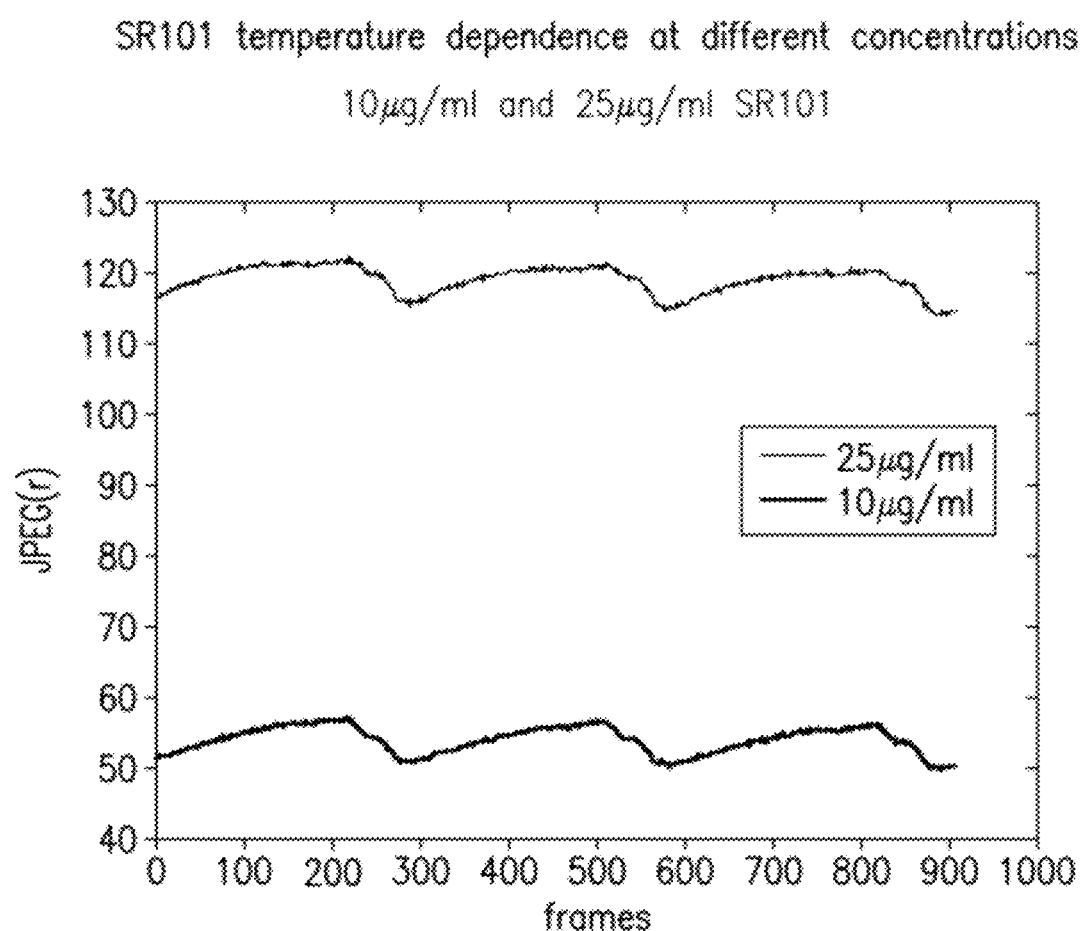
FIG. 6 is a plot of temperature dependence of a fluorescent dye embodying aspects of the present invention.
Figure 7:
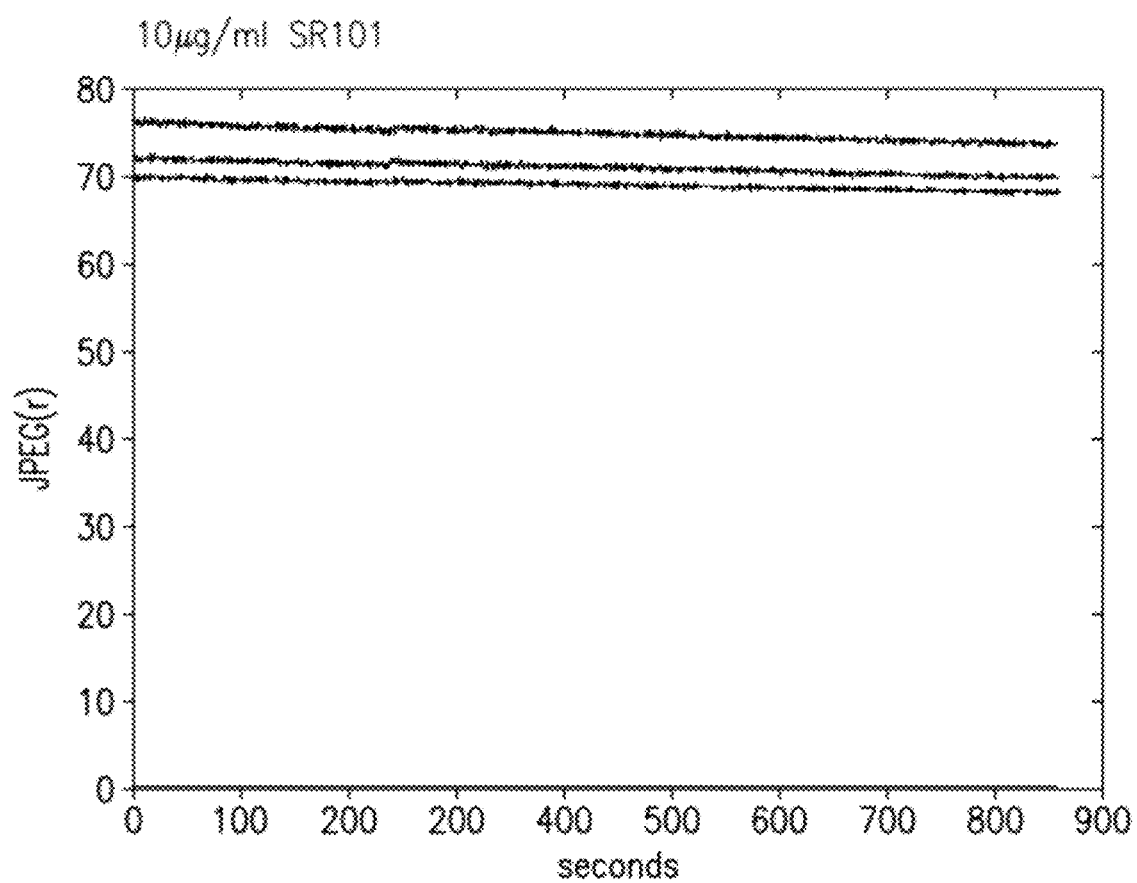
FIG. 7 is a plot of the photobleaching characteristics of a fluorescent dye embodying aspects of the present invention.

In another non-limiting embodiment, slug control can be realized during thermal cycling by including a dye in the blanking slug that is relatively insensitive to temperature change. The sample slug may still contain a temperature dependent dye. Examples of dyes with low temperature dependence include Fluorescien, HPTS, Rhodamine B, Sulforhodamine, Kiton Red, Texas Red, Phloxine B, LDS 698, 1-4 DHPN. Additional features of fluorescent dyes that are relatively insensitive to temperature change are described in "Dual emission laser induced fluorescence for direct planar scalar behavior measurements," J. Coppetta and B. Rogers, Experiments in Fluids Vol. 25 (1998), which is incorporated herein by reference. In some embodiments, the temperature insensitive dyes are also difficult to photobleach. Further, in preferred embodiments, the blanking dyes are chemically compatible with testing and sample materials (e.g., the dyes do not affect PCR, or any other reactions for which such devices are used). The temperature dependence and photobleaching characteristics of one such dye, Sulforhodamine 101, are illustrated in FIGS. 6 and 7. FIG. 6 shows the fluorescence of an exemplary slug containing 25 µg/ml of Sulforhodamine 101 and a second slug containing 10 µg/ml of the same dye over three temperature cycles from 20° C. to 90° C. Over that temperature range, the fluorescence intensity varies by approximately 11% for the 10 µg/ml sample, while the fluorescence intensity varies about 5% for the 25 µg/ml. FIG. 6 thus shows that Sulforhodamine 101 is a fluorescent dye that is relatively insensitive to temperature change. Likewise, FIG. 7 shows a graph of a 10 µg/ml sample of solution of Sulforhodamine 101 during exposure to a 0.1 A-powered LED (591 nm with 585/40 filter). In this example, over a period of 800 seconds, the fluorescence of the dye in the sample only decreased 3%, which indicates Sulforhodamine 101 is resistant to photobleaching.

Referring back to FIG. 3A and the process 300, at step 304, an image of the slug is acquired. In some embodiments, step 304 may be performed by the PCR zone flow monitoring system 218 acquiring an image of the microfluidic chip 100 from the detection device 222, or the fluorescence measurement system 232 acquiring an image of the microfluidic chip 100 from the measurement device 236. In one non-limiting embodiment, the imaging system may include a digital single lens reflex (DSLR) camera. In a non-limiting example, the DSLR camera may be the Canon 5DMkII. Other DSLR cameras that may be used in some embodiments include the Canon EOS-1Ds Mark III, Canon EOS-1D Mark IV, or other DSLR cameras.

In some embodiments, the imaging system may be operated in single frame mode (JPEG or raw mode) or in video mode using, for example, the LiveView feature. In some embodiments, the digital zoom provided by the DSLR camera can be used to provide one zoom or image position for flow control and another zoom or image position to perform functional analysis such as real time PCR or thermal melt analysis.

Figure 8:
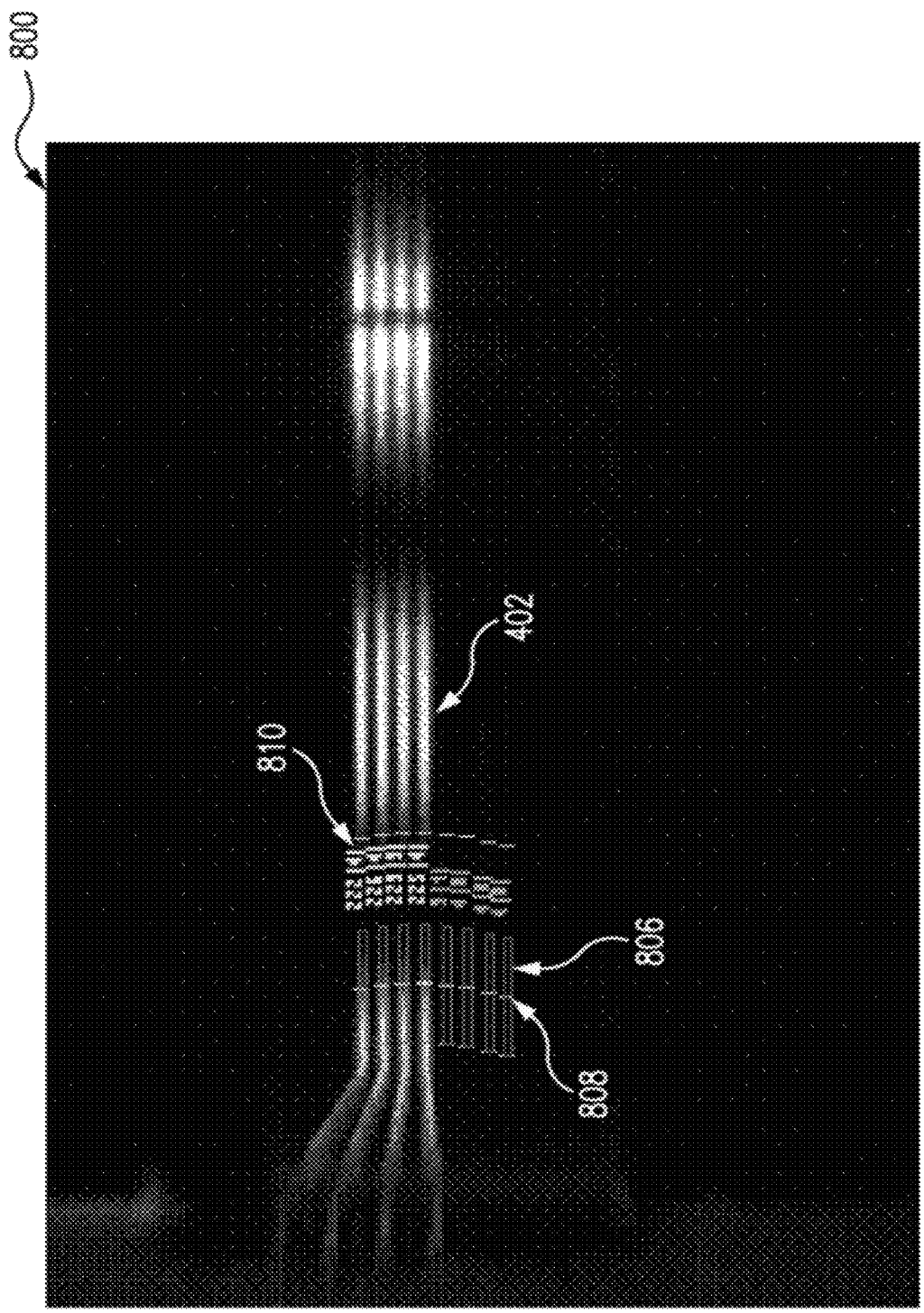
FIG. 8 is an image of fluorescing slugs in microfluidic channels of a microfluidic chip in accordance with aspects of the present invention.

FIG. 8 illustrates a non-limiting example of an image 800 that may be acquired at step 304 of process 300. The image 800 shows the fluorescence of slugs (e.g., blanking slugs 402) moving through channels, such as, for example, microfluidic channels 102.

In some embodiments, the fluorescent dye may fluoresce in a particular wavelength of light. This wavelength may be in any region of the electromagnetic spectrum, although it is preferable that it is in a region of the electromagnetic spectrum that can be detected or processed by the imaging system described above (e.g., the visible spectrum). To facilitate identification of the slugs, an image containing a range of wavelengths (e.g., a full color image) can be converted to an image containing a narrow band of wavelengths (e.g., a single color or grey scale image) representing fluorescence only in that particular wavelength range. For example, in embodiments using a dye that fluoresces strongly in red frequencies, a full color 24-bit RGB image can be converted to an 8-bit grayscale image using only the red plane of the RGB image.

The image 800 also illustrates ROIs 806 for slugs in each microfluidic channel. In the exemplary embodiment of FIG. 8, ROIs corresponding to eight microfluidic channels are illustrated, although only four of the channels contain fluorescing slugs. The center 808 of each ROI 806 is aligned with a target position for the respective slug, such as, for example, a leading edge for a blanking slug 402. Furthermore, in the non-limiting example of FIG. 8, each ROI may be labeled with numbers 810 indicating the maximum and/or minimum intensities within the ROI.

In some embodiments, the ROI size and the target position are determined based on the desired size of the slug. Preferably, the ROI should not be so large as to include more than one slug, because in some embodiments an ROI that includes more than one slug could "trick" the control system into controlling the wrong slug.

Figure 9:
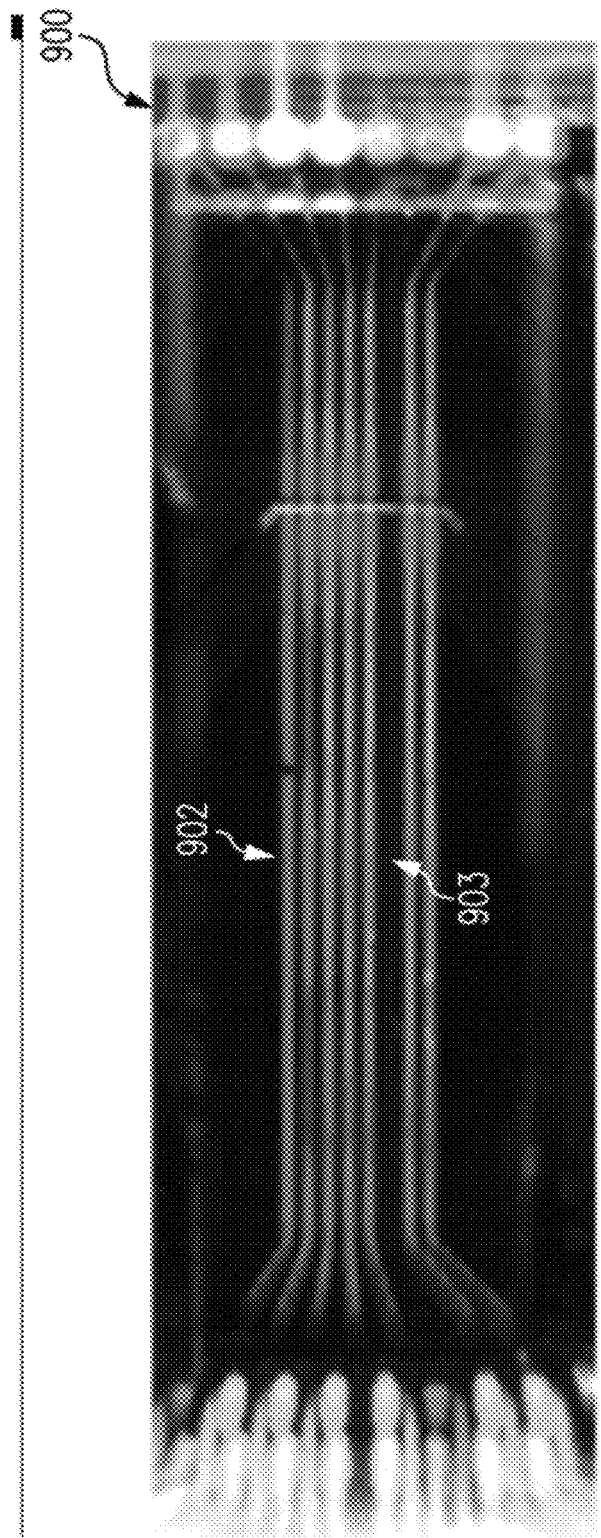
FIG. 9 is an image of fluorescing slugs in microfluidic channels of a microfluidic chip in accordance with aspects of the present invention

FIG. 9 illustrates another non-limiting example of an image acquired in accordance with step 304 of process 300. In particular, FIG. 9 illustrates image 900 wherein the top microchannel 902 was filled with blanking dye, and the sixth microchannel from the top 903 was left empty. The image 900 was acquired at a temperature of 25° C., with one red excitation source powered by 1.5 Amps of current, and one blue excitation source powered by 2.1 Amps of current. In this example, the remaining six channels show three blanking slugs (with Alexa Fluor 647) and three sample slugs (with LCGreen). In the example illustrated in FIG. 9, the saturation approach discussed earlier is applied to control slugs that thermally cycle in both PCR and thermal melt zones.

Figure 10:
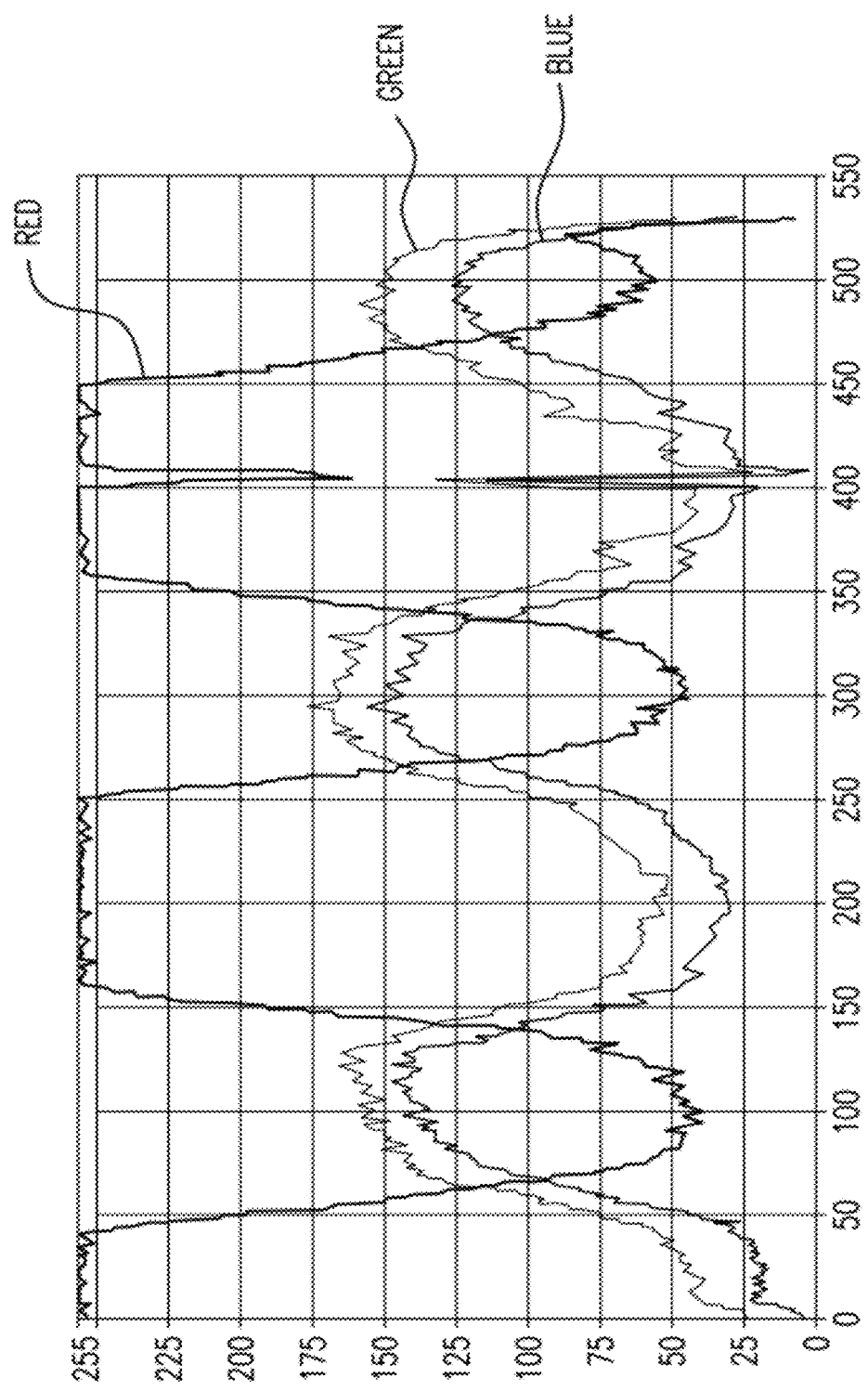
FIG. 10 illustrates intensity profiles slugs in a microchannel in accordance with aspects of the invention.

FIG. 10 illustrates intensity profiles for slugs along one of the channels illustrated in FIG. 9. As shown in FIG. 10, the red fluorescence of the blanking slugs has saturated the sensor (i.e., the amount of red fluorescence exceeds 255, the highest detectable value).

Referring back to FIG. 3A and the process 300, at step 306, one or more signal processing techniques can be applied to the ROIs, such as ROIs 806 of the image 800, to enhance the visibility of a slug 402 within each ROI.

In one non-limiting embodiment, the signal processing at step 306 includes a normalization process. Embodiments of the normalization process include scaling a threshold value, such as a threshold intensity value, based on a possible range of values observed in the ROI. In some embodiments, this value may be a threshold intensity value based on a possible range of intensities observed in the region of interest. Some embodiments can be implemented by analyzing fluorescence intensity values in the pixels of the image acquired at step 304 that correspond to the ROI, determining a peak intensity in the ROI, and then determining a scaling factor S required to bring that peak to the maximum intensity of the sensor (e.g., in an 8-bit image, determining the scaling factor S required to scale the maximum intensity in the ROI to 255). In some embodiments, the scaling factor S can be determined by dividing the maximum intensity of the sensor (e.g., 255 in an 8-bit sensor) by the maximum observed intensity in the ROI. The normalization process can then scale the intensity values in the entire region of interest, and then use a threshold intensity to determine the edge of a slug within the region of interest.

In some embodiments, the threshold intensity value may be set by the user. In these embodiments, the user may select an absolute value for the threshold intensity value, or may also select a relative intensity value, which may, for example, be a percentage of the maximum intensity. For example, in an embodiment where the user sets a relative intensity value that is a percentage of the maximum intensity, if a user sets a threshold of 50% in the software, the threshold intensity will be 127 (in an 8-bit system), and the edge of a slug will be detected where pixels cross that threshold (i.e., where pixels transition from values below 127 to values above 127). As a result of the normalization process, using a threshold intensity will not affect the process despite changes in absolute intensity of the fluorescence of the slug (e.g., through thermal cycling, increasing excitation power, etc). In some embodiments, it is preferable that the non-normalized intensity values are not saturated (e.g., provided that the initial intensity values do not exceed 255 in an 8-bit sensor system) such that the threshold value does not unduly effect the boundary determination. In some embodiments, the particles identified in the ROI by a threshold detection method may be filtered (by, in some non-limiting examples, using a low-pass spatial filter or a noise reduction filter) to smooth edges of the ROIs, which may facilitate slug control by ignoring dust or other image artifacts.

In another embodiment, the normalization method may also include scaling the minimum intensity as an alternative to, or in addition to, scaling the maximum intensity. In this case, the scaling factor S may be calculated from the span between the maximum and minimum intensities observed in the ROI. In this embodiment, it is preferable that the ROI include information corresponding to the microfluidic channel (e.g., the ROI be sized in such a way as to exclude dark pixels corresponding to areas outside the microchannel, or bright pixels caused by dust on the microfluidic chip).

Furthermore, in some embodiments the control system (e.g., the system 200) may be configured to check the span of intensities in the ROI to verify that a minimum span is present in the ROI. This feature is useful for determining whether a slug edge is present in the ROI because it can ensure that the slug control imaging system is not "tricked" by the normalization.

In another non-limiting embodiment, the normalization may use an average of the bright pixels in the ROI for determining the maximum intensity value in the ROI and an average of the dark pixels in the ROI for determining the minimum intensity value of the ROI. This can be implemented, for example, using a fixed number of pixels (e.g., the mean intensity of the brightest ten pixels) or using the distribution of intensities such as a histogram. For example, a histogram of intensities may be generated and the maximum intensity value for normalization may be the mode or median of the bright pixels. Conversely, the minimum intensity value for normalization may be the mode or median of the dark pixels.

In another embodiment, the normalization may include areas outside the region of interest for the purposes of determining the maximum intensity value and the minimum intensity value. This may be preferable when the slugs are smaller than the region of interest. In another embodiment, the normalization may use the maximum and standard deviation of intensity values for determining the appropriate threshold. In another non-limiting example, the normalization approach may use National Instrument's Labview software which includes an auto-thresholding function.

In a non-limiting embodiment, the signal processing at step 306 may include a color thresholding process. That is, in some embodiments, the slugs can be controlled by determining the edges or slug positions using more than one color plane of the image acquired at step 304. Embodiments including these features may be useful when the colors used in adjacent slugs are similar or appear similar because of the imaging system (e.g., cross-talk). National Instrument's Labview software includes a color thresholding function that may be appropriate for some embodiments.

In further embodiments, other methods of thresholding may involve generating a histogram (or other accounting of pixel intensity values), determining two populations of pixel intensities (e.g. one for dark pixels that are not part of the slug and one for bright pixels that are part of the slug), and setting a threshold at a point between the two populations (e.g., half way between the mean pixel values for each population).

In another embodiment, a method of color thresholding may involve using two color planes (e.g., blue and red in FIG. 9) to obtain two measures of slug position: one based on the position of the sample slugs (e.g., blue slugs) and one based on the blanking slugs (e.g., the red slugs). Making two measures of slug position is advantageous since the two measures can be averaged to determine the best estimate of position and the two measures give an estimate of the error associated with slug position. In a non-limiting embodiment using LCGreen dye (which fluoresces at a wavelength that may be recognized by an image processing system as both green and blue pixels) in a slug, the blue and green color planes could be used to determine the position of the slug with LCGreen dye (i.e., averaging could be used). More than two color planes could be used in some embodiments. In a non-limiting example, an Alexa Fluor 647 slug could be measured using the red plane and an adjacent LCGreen slug could be measured with both the blue and green planes.

In one non-limiting example of when such a color thresholding process may be useful, a sample slug may fluoresce primarily blue and green in color but also may have a component that fluoresces red as well. On the other hand, a blanking slug adjacent or nearby to the sample slug may fluoresce primarily in red but also may fluoresce some blue and green components. In this case, both the blanking slugs and the sample slugs fluoresce at least partially in each color plane (e.g., in each of red, green, and blue wavelengths). Such a case would normally be difficult to control because it is difficult for a controller to distinguish, for example, which slugs are red blanking slugs. In some embodiments, the difficulty may be increased under flow and thermal cycling conditions. Applying color thresholding, a sample slug can be found by specifying a minimum blue and/or a minimum green value. Further, sample slugs can also be specified to have a maximum red value. A blanking slug can be found by specifying a minimum red value and/or maximum blue and/or green values. In this manner, all color information is used and the controller can easily distinguish the two types of slugs. The specific combination of colors for identifying blanking slugs and sample slugs is dependent on the particular embodiment (e.g., which dyes are used for the blanking and sample slugs). In some embodiments, this method could be extended to discriminate between various slug types (e.g., blanks, sample A, sample B, etc.).

In a non-limiting embodiment, the signal processing at step 306 includes a temperature-based intensity correction. In some embodiments, software or specially configured hardware can be used to correct the observed fluorescence intensity using the system temperature. In this embodiment, the physical fluorescence intensity does not need to be directly manipulated (e.g., by light modulation as described above). Rather, the observed fluorescence intensity may be scaled as a function of the measured temperature, resulting in an approximately temperature insensitive fluorescence intensity. In another embodiment, the threshold can be varied as a function of the measured, or known, temperature.

Referring back to FIG. 3A, at step 308, the position of a slug is identified within each ROI. In some embodiments, step 308 can include identifying the location of a center, edge or other feature of a slug within each ROI.

In a non-limiting embodiment, step 308 includes an accounting for thermal expansion of the slugs. In some embodiments, the sample and blanking liquids expand and contract during thermal cycling or other temperature changes due to the changing densities of liquids. In one embodiment, the magnitude of this expansion and contraction can be predicted based on the following relation which assumes the cross-section of the channel is constant:

$$\Delta l = l_1 \left( \frac{\rho_1}{\rho_2} - 1 \right) \qquad \text{Equation 1}$$

In Equation 1, $l_1$ is the length of the slug at a first temperature, $\rho_1$ is the density of the slug at the first temperature, $\rho_2$ is the density of the slug at a second temperature, and $\Delta l$ is the change in the length of the slug between the first and second temperature. In one non-limiting example, heating is confined to a PCR zone that is 14.75 mm in length, and a slug within that PCR zone may expand approximately 360 microns when heated from 55° C. to 95° C. In another non-limiting example, heating is confined to a thermal melt analysis zone that is 4.65 mm in length and a slug may expand 90 microns when heated from 65° C. to 95° C. The densities of the slugs at the first and second temperature may be estimated from the variation of the density of the solvent used to form the slugs (e.g., water) with temperature. Again, these sizes and functional zones are merely used as illustrations of how a slug length may expanded when heated and are not intended to be limiting.

In some embodiments, the location of the expansion may be related to where the slug edge is controlled relative to the thermal control element(s). For example, if the control position is in the center of a PCR zone, then the expansion will be evenly distributed to the right and left about the control position (i.e., the expansion will be distributed along the thermal control element). Alternatively, if the control position is on the left side of a PCR zone, then the expansion will primarily be on the right side (i.e., the expansion primarily will be into the PCR zone heated by the thermal control element). In one embodiment, the slug control system is updated at a frequency that is much faster than any concomitant thermal cycling, such as PCR thermal cycling, In another embodiment, the thermal expansion of the slugs is used to better control slugs. By calculating and using the expected thermal expansion of a slug, one can design an appropriate slug detection algorithm that minimizes system response to thermal expansion. For example, a slug that is uniformly heated (e.g., a slug that is centered over a heated zone) will expand about its center. Therefore, in some embodiments, the slug's center may be tracked so that the controller does not respond to the thermal expansion. In another embodiment, two or more points on opposite sides of the center of the slug could be tracked such that their average position is representative of the center of the heated zone. In this manner, the slug control will not attempt to follow the thermal expansion since an equal amount of expansion occurs in each direction (i.e., the expansion to the left will negate the expansion to the right as the two edges are observed moving away from each other, so the average position of the two edges does not move).

In some embodiments, tracking the slug's center is preferable because the center of the slug is identifiable regardless of how the intensity varies (i.e., the center is robust against changes in intensity due to temperature variation). In some embodiments, large ROIs relative to the size of the slugs may be used to track the centers of the slugs (which may be relatively small).

Referring back to FIG. 3A and the process 300, in a non-limiting embodiment, step 308 may include correlation methods, such as, for example, calculating a cross-correlation and covariance with a template, rather than threshold detection. An advantage of using cross-correlation to determine the slug boundaries is that more image information may be used than in the threshold approach. This method may be used to detect edges of slugs or entire slugs. In one non-limiting embodiment, a simple binary image (black on one side and white on the other) is used to detect an edge of a slug. The transition from the black side to the white side of the template represents the slug edge. The black/white template image is then cross-correlated with the slug images to determine the location of the slug edge (i.e., the position at which the correlation between the template and the ROI image data is at a maximum or minimum).

Figure 11:
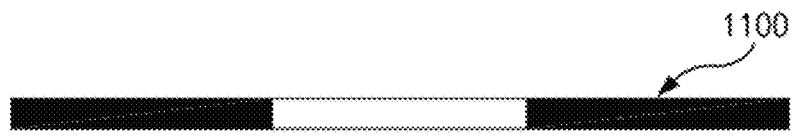
FIG. 11 is a template image for cross correlation embodying aspects of the present invention.

One example of such a method for cross-correlation is a two-dimensional, normalized cross-correlation for detection of a smaller image (e.g., the template) within a larger image (i.e, image pattern matching). In one embodiment, the template image contains a light region in between two dark regions; alternately, the template image may contain a bright region between two dark regions. Using such a template image may be robust to the degree of change in brightness from non-slug to slug, or vice versa. Using such a template image may, in some embodiments, obviate the need to choose an intensity threshold, and may thus be robust with changes in light source intensity. Another method of tracking multiple moving objects in a series of images may include the Lucas-Kanade method, which is described in B. D. Lucas and T. Kanade, "An iterative image registration technique with an application to stereo vision," Proceedings of Imaging Understanding Workshop, 121-130 (1981), and Bruce D. Lucas, "Generalized Image Matching by the Method of Differences," doctoral dissertation, tech. report, Robotics Institute, Carnegie Mellon University, (July, 1984), both of which are hereby incorporated by reference in their entirety. Another example of a method of tracking multiple moving objects in a series of images is the Horn-Schunck method, which is described in B. K. P. Horn and B. G. Schunck, "Determining optical flow." 17 Artificial Intelligence 185-203 (1981), hereby incorporated by reference in its entirety. In some embodiments, more than one slug can be used in the correlation. For example, the center of a slug could be controlled using a template image 1100, as illustrated in FIG. 11. FIG. 11 is an image with two black regions surrounding a white region; by determining where the correlation between that image and the image of the slugs is the greatest, one may detect light-to-dark-to-light transitions within the image of the slugs, and thus the locations of the slugs themselves.

In another embodiment, where the length of the slug is variable or unknown, one may use a half/half template. Such a half/half template image may be, in some embodiments, half light and half dark, i.e. half of the template is a dark region and half of the template is a light region. The length of each template region should be the smallest expected length of each slug that is to be identified. In an exemplary template, the left half may be black and the right half may be white, or vice versa. When the template is cross-correlated against the image of the entire length of the microfluidic channel, it may generate a cross-correlation value between negative one and one. When the cross-correlation value is close to 1, the system may determine that a left edge of a slug has been found, and whenever the cross correlation value is close to −1, the system may determine that a right edge has been found. Using such a template image and image cross-correlation, the edges of multiple slugs can be found by the system. In the case where the left half of the template is white and right half is black, the signs of the cross-correlation vector may be reversed, but the principle of operation will remain the same. The middle of the one or multiple slugs can be found by taking the midpoint of each detected left edge and right edge. To detect multiple slugs using normalized cross-correlation, in one non-limiting embodiment, two images may be used: a smaller and a larger image. In a non-limiting example, the smaller image may be a half black/half white image, where the length of a particular light or dark region is the minimum expected length of a single slug, and the larger image may be the length of the entire microfluidic channel or ROI within, as described above.

Referring back to FIG. 3A, at step 310 of process 300, after the current position of each slug 402 has been determined, each slug 402 can be moved to a desired target position. In some embodiments, steps 302 through 310 can be repeated at a regular rate (e.g., 1 Hz) to provide adequate feedback for a closed loop control system for the movement of the slugs. For example, in some embodiments, the flow controller 208 may use a proportional integral derivative ("PID") control scheme to command pumps to drive the slug to the desired target position. Those of skill in the art will understand that alternate control schemes to PID control can also be used as appropriate to the application. However, any appropriate control scheme may be useful in conjunction with the present invention; for example, in some embodiments, an ON/OFF control scheme may be used.

In some non-limiting embodiments, the control of the slugs can be modulated by reducing or enhancing the system's response to apparent movement of the slugs. In one embodiment, this can include adjusting PID control parameters for different steps in a thermal cycle or thermal heating pattern (e.g., a PCR thermal cycle). For example, the gain can be reduced during large temperature changes. In another embodiment, control of the slugs can be turned off during some temperatures. This may be preferable in extreme temperatures or temperatures that are maintained for short periods. For example, in a rapid PCR process, the denaturation step can be quite short. It may be desirable during such a short denaturation step not to attempt any control of the slugs. In some embodiments, this may also include not acquiring images with the image control system during these portions of the reaction. Alternatively, the light source used to drive sample fluorescence could be turned off during these portions.

In some embodiments, the control system moves the slugs 402 along the microchannel 102 by alternating between holding the leading and trailing edges of blanking slugs. Through this alternating process, a series of slugs can be controlled forming a "slug train." In some embodiments, the ROIs 406 are moved along at a steady velocity to smoothly move with the slugs 402 along the channel 102. Moreover, in some preferred embodiments, the control process for each channel 102 can be performed in parallel.

Figure 12:
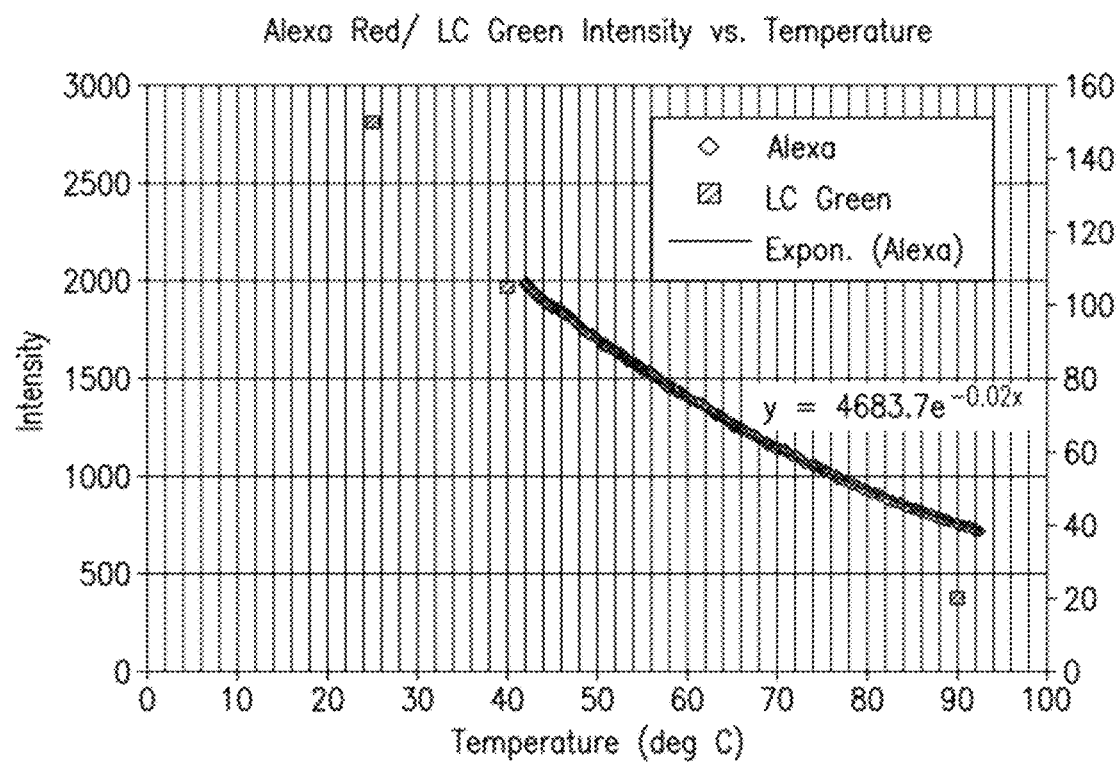
FIG. 12 is a plot of fluorescence intensity as a function of temperature for certain fluorescent dyes embodying aspects of the present invention.

In some cases, the dyes that may be used in some aspects of the methods of the present invention may be strongly temperature dependent. In the case of a strongly temperature dependent dye, certain errors may be introduced when measuring fluorescence at high temperatures, as fluorescence tends to decrease with temperature in such dyes. FIG. 12 is a plot of fluorescence intensity as a function of temperature (i.e., F vs. T) for an Alexa red dye and an LCGreen dye. As illustrated in FIG. 12, the fluorescence of these dyes can change by a factor of two or more over the range of temperatures typically used for PCR amplification and thermal melt analysis. The dyes generally tend to lose their fluorescence intensity when heated, and gain fluorescent intensity when cooled. In certain high-temperature applications (e.g., PCR) it may be necessary to measure slug fluorescence at high temperatures (e.g., during a denaturation step of PCR). In some embodiments, one may account for the decrease in fluorescence at high temperatures by deriving a functional relationship between the fluorescence of the dye and the temperature of the dye at lower temperatures (using, e.g., a data set such as that displayed in the graph of FIG. 12) and extrapolating that relationship to higher temperatures.

Another aspect of the invention may include a method for controlling the position of a sample slug in a microfluidic device which is surrounded by blanking slugs. In one embodiment, the method may comprise providing a first blanking slug including a fluorescent dye and a second blanking slug including a fluorescent dye, wherein said first and second blanking slugs surround the sample slug; exciting a fluorescent dye in the blanking slugs; acquiring an image of the blanking slugs and sample slug, wherein the image captures the fluorescence of the blanking slugs; processing data from a region of interest in the image; identifying a position of the sample slug within the region of interest from the processed image data; and controlling the position of the sample slug based on the identified position of the sample slug. In a further embodiment, the sample slug may contain little or no fluorescent dye. Alternately, the sample slug may contain a dye that fluoresces at a first wavelength, and the first and second sample slugs may each contain a dye that fluoresces at a second wavelength, and the first and second wavelength are different.

Alternately, another aspect of the invention may include a method for controlling the position of a sample slug in a microfluidic device, comprising providing a blanking slug comprising a fluorescent dye, wherein the blanking slug has an interface with the sample slug, exciting a fluorescent dye in the blanking slug; acquiring an image of at least a portion of the blanking slug and at least a portion of the sample slug; processing data from a region of interest in the image; identifying a position of the sample slug within the region of interest from the processed image data; and controlling the position of the sample slug based on the identified position of the sample slug.

Figure 3B:
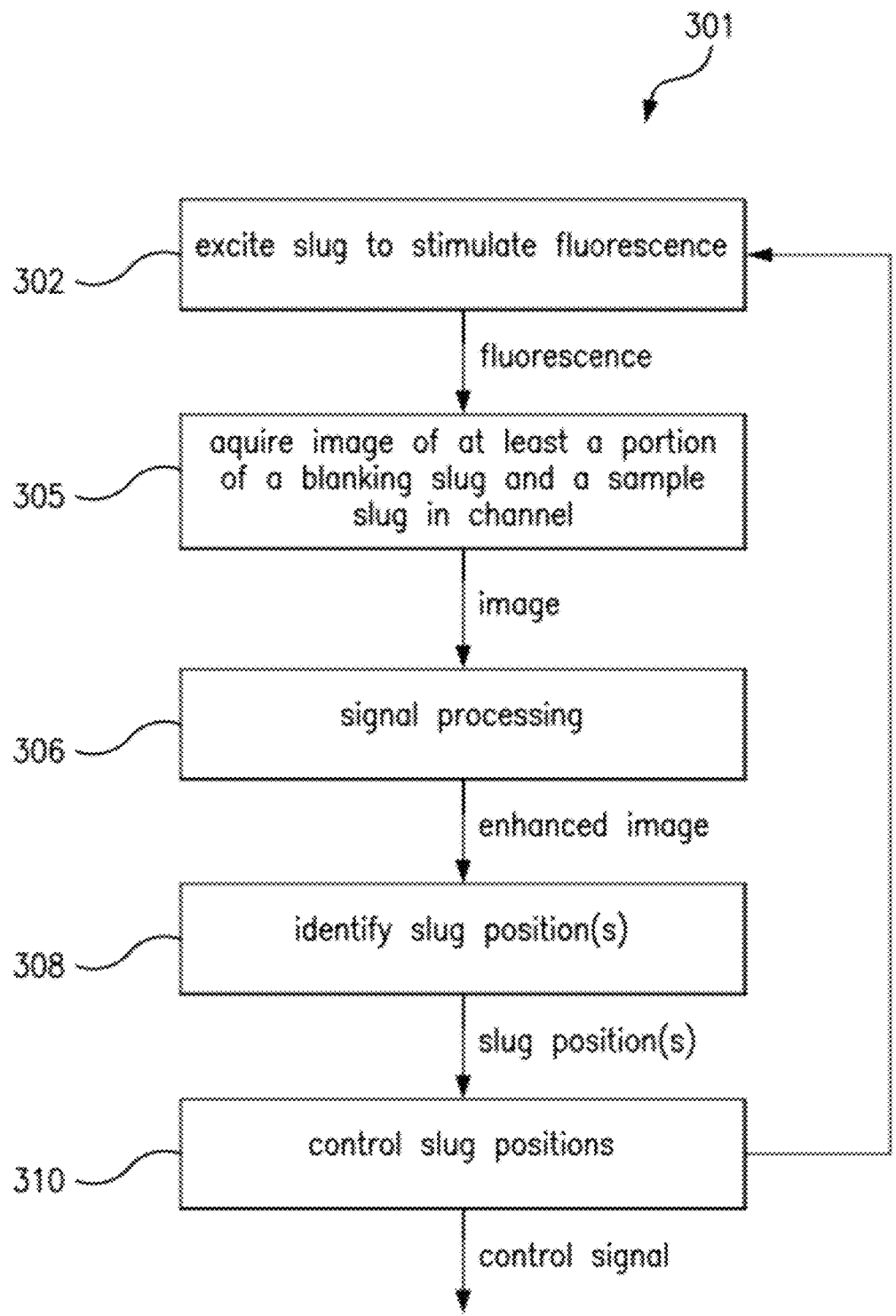
FIG. 3B illustrates a process for controlling one or more slugs in accordance with embodiments of the invention.

An embodiment of these methods for tracking a sample slug may be described in connection with FIG. 3B. In one embodiment of method 301, step 302 may include exciting fluorescence in one or both blanking slugs 402 surrounding a sample slug 404 in a microfluidic device, such as microfluidic channel 102. In a further embodiment, step 302 may include not exciting fluorescence in the sample slug. This may be accomplished by including little to no fluorescent dye in the sample slug. In an alternate embodiment, the method may include exciting fluorescence in the one or both blanking slugs with a wavelength of light that does not stimulate fluorescence in a fluorescent dye contained in the sample slug. In another embodiment, the sample slug may contain a fluorescent dye that fluoresces a wavelength of light that is significantly different than the wavelength of light fluoresced by the dye in the blanking slugs. In this embodiment, a detector device 222 or 226 may only detect light in the wavelengths at which the dye in the blanking slug fluoresces. In some embodiments, the microfluidic device may incorporate detector devices to detect fluorescence from the blanking slugs versus the sample slugs, or different light sources to stimulate fluorescence in the dyes in the blanking and sample slugs. In any of these embodiments, the sample slugs may register as dark portions within the channel.

In step 305 of method 301, the image acquisition device may acquire an image of the blanking slugs in the channel using the image acquisition methods described above. In one embodiment, the sample slug appears as a dark slug in between the fluorescing blanking slugs, or next to a fluorescing blanking slug. This may be accomplished by not stimulating fluorescence in the sample slug in step 302, through the methods described above. Alternately, in step 305, only an image of the fluorescence of the blanking slugs (and not the fluorescence of the sample slug) may be acquired. This may be accomplished through using an image detection system that only detects fluorescence in the wavelengths of the blanking slugs, which again will have the effect of leaving the sample slug as a dark spot in between two fluorescing blanking slugs in the acquired image. Alternatively, step 305 may be performed by acquiring an image of at least a portion of one of the blanking slugs and at least a portion of the sample slug, including the interface between the at least one blanking slug and the sample slug, with the sample slug appearing as a dark region next to the fluorescing blanking slug.

In step 306 of the method 301, the image signal may be processed. In this embodiment, signal processing may include methods for enhancing the visibility of the fluorescing blanking slugs versus the dark sample slug, such as the normalization, color thresholding, and temperature-dependent fluorescence detection approaches described herein. In step 308, the sample slug or blanking slug positions may be detected. If the sample slug's position is detected, the center or the edges of the dark sample slug, relative to the fluorescing blanking slug(s), may be detected using the methods described above. Alternately, the center of the dark sample slug may be detected using the methods described above. In the instance where the image includes at least a portion of one of the blanking slugs and at least a portion of the sample slug, including the interface between the at least one blanking slug and the sample slug, step 308 may include detecting the interface and defining it as the edge of one of the slugs, and may also include tracking that edge. Finally, in step 310, the sample slug position may be controlled, using any of the methods for controlling slug position described earlier in this application.

In other aspects, the present invention may include a system for controlling the position of a slug within a microfluidic device. The system may include a microfluidic device that includes one or more fluid channels. An example of such a microfluidic device is device 100 shown in FIG. 1, although those of skill in the art will recognize that the system may include any microfluidic device that includes one or more channels. The system may also include one or more slugs in the one or more fluid channels. Those slugs, in some embodiments, may include sample slugs 404, blanking slugs 402, or other varieties of slugs, such as a calibration slug, or any other variety of slug that can reasonably be used in conjunction with a microfluidic channel.

Aspects of the system may include a light-sensing unit adapted to capture light from at least a region of interest of the microfluidic device. In one embodiment, this light-sensing unit may be any sensor adapted to receive light signals and convert them into information for use in the remainder of the system, such as a photoresistor, a digital single-lens reflex (DSLR) camera, or other light-sensing device. In some embodiments, the fluorescence detector 222 or 236 may be the light-sensing unit. The fluorescence detector itself may be any sensor adapted to receive light signals and convert them into information for use in the remainder of the system, such as a photoresistor, a DSLR camera. This light-sensing unit may capture light (which may be reflected light, transmitted light, fluorescence, etc.) from the microfluidic device within a region of interest (ROI) that includes one or more of the slugs.

The system may further include a processing unit. This processing unit may be adapted to receive information from the light-sensing unit, and is preferably adapted to transmit such information to a position identification unit. The processed information transmitted by the processing unit is used to identify the position of a slug within the ROI. In some embodiments, both the processing unit and the position identification unit may be one or more appropriately programmed computers. Alternately, the processing unit may be a circuit adapted to receive signals from the light-sensing unit and transmit such information to an appropriately programmed computer acting as the position identification unit, or to transmit a processed signal to an appropriately designed circuit acting as the position identification unit, which is adapted to identify the position of a slug within the microfluidic device.

The position identification unit may generate information or a signal useful in identifying the position of the slug within the microfluidic device. The position identification unit may be in communication with a slug control unit, which is adapted to position the slug within the microfluidic device based upon the identified position. The slug control unit may include multiple components, such as an appropriately programmed computer in combination with a slug movement device operatively engaged with the microfluidic device to move the slug or slugs within the microfluidic device. In one embodiment, the slug movement device may be a pump operatively engaged with the microfluidic device. The slug movement device, however, can be any device engagable with a microfluidic device and capable of moving the slugs within the device, non-limiting examples of which include a syringe driver, a pipettor, a peristaltic pump, or an electroosmotic system. The slug movement device may be controlled by an appropriately programmed computer. The appropriately programmed computer of the slug control unit may include a proportional-integral-derivative control algorithm designed to receive information from the position identification unit and adapted to identify when the slug is properly or improperly positioned. If the slug is improperly positioned, the algorithm may move the slug into a proper position by instructing the slug movement device to move the slug within the microfluidic channel.

In one embodiment, the system may further include a slug excitation device adapted to excite the one or more fluorescent dyes within the one or more slugs. In one embodiment, the slug excitation device may be the slug excitation device 220 or 234 shown in FIG. 2. In another embodiment, the slug excitation device may be a light source of sufficient intensity and of an appropriate wavelength to cause a fluorescent dye within the slug to fluoresce. The slug's fluorescence may then be detected by the light-sensing unit of the system.

In one embodiment, the system may further include thermal elements in the microfluidic device. In one non-limiting embodiment, these thermal elements may be heaters 112 in communication with microchannel 102. In a further embodiment, the system may include a temperature control unit configured to control the temperatures of the slugs within the microfluidic device. In one non-limiting embodiment, this temperature control unit may include PCR zone temperature controller 210, which may operate in conjunction with a temperature sensor 214 and heating and cooling units 212 and 214.

In one embodiment, the temperature control unit may be configured to subject the slug to a thermal cycle. One non-limiting example of such a thermal cycle includes a denaturation step at a first temperature for a first duration of time, an annealing step at a second temperature for a second duration of time, and an extension step at a third temperature for a third duration of time. One non-limiting example of such a thermal cycle includes a denaturation step having a duration of about one second, an annealing step having a duration of about eight seconds, and an extension step has a duration of about one second. The temperatures and times for these steps are discussed in reference to other aspects of the present invention.

In one embodiment of the present invention, the duration of the denaturation step is shorter duration than the period between image acquisitions. Alternately, in another embodiment of the invention, the duration of the annealing step is longer than the duration of the denaturation step and at least a portion of the images acquired for slug control are acquired during the annealing step.

In one alternate embodiment, the duration of the extension step is longer than the duration of the denaturation step, and at least a portion of the images are acquired during the extension step.

Alternately, rather than using a three-step thermal cycle, in one embodiment of the invention, the temperature control unit may be configured to subject said slug to a two-step cycle. Such a two-step cycle may include a denaturation step at a first temperature for a first duration of time, and an annealing/extension step at a second temperature for a second duration of time. The temperatures and times, again, are discussed in reference to other aspects of the present invention.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method for controlling the position of a slug in a microfluidic device, comprising:
   (a) providing a slug in a microfluidic channel of the microfluidic device;
   (b) exciting a fluorescent dye in said slug;
   (c) acquiring an image including a portion of the microfluidic channel having the slug emitting the fluorescence and a portion of the microfluidic channel without the slug;
   (d) processing intensity profile data from a region of interest in said image, wherein the region of interest encompasses a portion of the microfluidic channel without the slug, the intensity profile data including fluorescence intensity presented as a function of a position along the microfluidic channel;
   (f) identifying a position of said slug within said region of interest from said intensity profile data;

(e) controlling the position of said slug within the microfluidic channel by moving the slug to a target position based on the identified position of said slug in said microfluidic channel; and (g) repeating steps (b)-(e) at a regular rate while the slug is moving along the microfluidic channel.

2. The method of claim 1, wherein said step of exciting a fluorescent dye in said slug comprises exposing said slug to a light source of sufficient power such that the fluorescence of said dye will exceed a maximum intensity value of said image.

3. The method of claim 1, further comprising measuring a state of said slug, and wherein said step of exciting a fluorescent dye in said slug comprises modulating the output of an excitation source in response to a measured state of said slug.

4. The method of claim 3, wherein modulating the output of an excitation source comprises modulating the power of the excitation source, and wherein said measured state of said slug is the temperature of said slug.

5. The method of claim 1, wherein said step of exciting a fluorescent dye in said slug comprises exposing a region of said slug to a high intensity light source.

6. The method of claim 1, further comprising the step of photobleaching a portion of said slug and wherein said step of identifying the portion of said slug comprises identifying the photobleached portion of said slug.

7. The method of claim 1, wherein said step of processing data in a region of interest in said image comprises scaling intensity values in said region of interest such that the maximum intensity value in said region of interest is scaled to be the maximum intensity value for said image.

8. The method of claim 1, further comprising measuring a state of said slug, and wherein said step of processing data in a region of interest in said image comprises scaling intensity values in said region of interest in response to a measured state of said slug.

9. The method of claim 8, wherein said measured state is temperature of the slug.

10. The method of claim 1, wherein said step of identifying a position of said slug within said region of interest comprises identifying pixels that satisfy threshold conditions in two or more wavelength planes of said image.

11. The method of claim 1, wherein said step of identifying a position of said slug within said region of interest comprises using information about the predicted thermal expansion of the slug to identify a position of said slug.

12. The method of claim 1, wherein said step of identifying a position of said slug within said region of interest comprises cross-correlating said region of interest with a predetermined template image.

13. The method of claim 1, wherein said step of identifying a position of said slug within said region of interest comprises identifying two or more points of said slug and averaging the positions of said two or more points.

14. The method of claim 1, wherein said step of controlling the position of said slug comprises using a proportional-integral-derivative control device to move the slug based upon its identified position.

15. The method of claim 1, wherein said step of controlling the position of said slug comprises modulating a control element operatively engaged with said microfluidic device based on an expected or measured state of said slug.

16. The method of claim 1, wherein the fluorescence of said dye is relatively insensitive to temperature change.

17. The method of claim 1, wherein said slug undergoes changes in temperature.

18. The method of claim 1, wherein the target position of a slug is a desired position for a leading edge of a blanking slug.

19. A method for controlling the position of fluid slugs in a microfluidic device, comprising:

(a) providing a first slug in a microfluidic channel in said microfluidic device, wherein said first slug comprises a first dye;

(b) providing a second slug in a microfluidic channel in said microfluidic device, wherein said second slug comprises a second dye;

(c) acquiring an intensity profile image of the microfluidic channel comprising said first and second slugs in said microfluidic device, processing intensity profile data from a region of interest in said image, the intensity profile data including fluorescence intensity presented as a function of a position along the microfluidic channel;

(d) identifying a boundary between said first slug and said second slug and the position of the boundary within said region of interest from said processed image data;

(e) controlling the position of said first slug and said second slug within the microfluidic channel by moving the first and second slugs to a target position based on the identified boundary between said slugs in said microfluidic channel; and (f) repeating steps (c)-(e) at a regular rate while the slug is moving along the microfluidic channel.

20. The method of claim 19, wherein one of said first slug or said second slug is a sample slug containing a biological sample to be processed and/or analyzed, and the other of said first or said second slug is a blanking slug containing no sample to be processed and/or analyzed.

21. The method of claim 19, wherein said first dye is a fluorescent dye that fluoresces at a first wavelength of light, and wherein said second dye is a fluorescent dye that fluoresces at a second wavelength of light.

22. The method of claim 21, further comprising the step of exciting fluorescence in said first and second fluorescent dyes in said first and second slugs.

23. The method of claim 22, wherein said step of identifying a boundary between said first and said second slugs within said region of interest comprises identifying pixels that satisfy threshold conditions in a first wavelength plane of said image and a second wavelength plane of said image.

24. The method of claim 23, wherein said step of identifying a boundary between said first slug and said second slug within said region of interest comprises cross-correlating said region of interest with a predetermined template image.

25. A method for controlling the position of a slug in a microfluidic channel of a microfluidic device, comprising:

(a) acquiring an intensity profile image including a portion of the microfluidic channel having a slug and a portion of the microfluidic channel without the slug;

(b) processing intensity profile data from a region of interest in said image, wherein the region of interest encompasses a portion of the microfluidic channel without the slug, the image data including fluorescence intensity presented as a function of a position along the microfluidic channel;

(c) identifying a position of said slug within said region of interest from said intensity profile data;

(d) controlling the position of said slug within the microfluidic channel by moving the slug to a target position based on the identified position of said slug in said microfluidic channel; and (e) repeating steps (a)-(d) at a regular rate while the slug is moving along the microfluidic channel.

26. The method of claim 25, wherein said slug comprises a fluorescent dye and further comprising the step of exciting said fluorescent dye in said slug.

27. A method for controlling the position of a sample slug in a microfluidic device, comprising:
(a) providing a first blanking slug comprising a fluorescent dye and a second blanking slug comprising a fluorescent dye, wherein said first and second blanking slugs surround said sample slug in a microfluidic channel;
(b) exciting a fluorescent dye in said blanking slugs;
(c) acquiring an intensity profile image of the microfluidic channel comprising said blanking slugs and said sample slug, wherein the image captures the fluorescence of the blanking slugs;
(d) processing intensity profile data from a region of interest in said image, the image data including fluorescence intensity presented as a function of a position along the microfluidic channel;
(e) identifying a position of said sample slug within said region of interest from said processed intensity profile data;
(f) controlling the position of said sample slug within the microfluidic channel by moving the slug to a target position based on the identified position of said sample slug in said microfluidic channel; and
(g) repeating steps (b)-(f) at a regular rate while the slug is moving along the microfluidic channel.

28. The method of claim 27, wherein said sample slug contains little or no fluorescent dye.

29. The method of claim 27, wherein said sample slug contains a dye that fluoresces at a first wavelength, and said first and second sample slugs each contain a dye that fluoresces at a second wavelength, wherein said first and second wavelength are different.

30. A method for controlling the position of a sample slug in a microfluidic device, comprising:
(a) providing a first blanking slug comprising a fluorescent dye and a sample slug, wherein said blanking slug has an interface with said sample slug in a microfluidic channel;
(b) exciting a fluorescent dye in said blanking slug;
(c) acquiring an intensity profile image of the microfluidic channel comprising at least a portion of said blanking slug and at least a portion of said sample slug;
(d) processing intensity profile data from a region of interest in said image, the intensity profile data including fluorescence intensity presented as a function of a position along the microfluidic channel;
(e) identifying a position of said sample slug within said region of interest from said processed intensity profile data;
(f) controlling the position of said sample slug within the microfluidic channel by moving the slug to a target position based on the identified position of said sample slug in said microfluidic channel; and
(g) repeating steps (b)-(f) at a regular rate while the slug is moving along the microfluidic channel.

* * * * *